US007622277B2

(12) United States Patent
Rehm

(10) Patent No.: US 7,622,277 B2
(45) Date of Patent: Nov. 24, 2009

(54) PROCESS FOR THE PRODUCTION OF BIODEGRADABLE, FUNCTIONALISED POLYMER PARTICLES, AND USE THEREOF AS PHARMACEUTICAL SUPPORTS

(75) Inventor: Bernd Helmut Adam Rehm, Palmerston North (NZ)

(73) Assignee: Massey University, Palmerston North (NZ)

( * ) Notice: Subject to any disclaimer, the term of this patent is extended or adjusted under 35 U.S.C. 154(b) by 0 days.

(21) Appl. No.: 10/525,955

(22) PCT Filed: Aug. 22, 2003

(86) PCT No.: PCT/DE03/02799

§ 371 (c)(1),
(2), (4) Date: Mar. 31, 2006

(87) PCT Pub. No.: WO2004/020623

PCT Pub. Date: Mar. 11, 2004

(65) Prior Publication Data

US 2006/0160194 A1 Jul. 20, 2006

(30) Foreign Application Priority Data

Aug. 30, 2002 (DE) ............................... 102 40 035

(51) Int. Cl.
*C12P 1/00* (2006.01)
(52) U.S. Cl. ....................................................... 435/41
(58) Field of Classification Search .................... 435/41
See application file for complete search history.

(56) References Cited

U.S. PATENT DOCUMENTS

| 5,405,752 | A | 4/1995 | Nilsson |
| 5,610,041 | A | 3/1997 | Somerville et al. |
| 5,738,986 | A | 4/1998 | Nilsson |
| 6,022,729 | A | 2/2000 | Steinbuchel et al. |
| 6,103,956 | A | 8/2000 | Srienc et al. |
| 6,146,665 | A | 11/2000 | Marchessault et al. |
| 6,835,820 | B2 | 12/2004 | Cannon et al. |
| 7,169,589 | B2 | 1/2007 | Muller et al. |
| 2003/0134391 | A1 | 7/2003 | Mueller et al. |

FOREIGN PATENT DOCUMENTS

| WO | WO 97/22711 A1 | 6/1997 |
| WO | WO 99/20256 | 4/1999 |
| WO | WO 99/35278 | 7/1999 |
| WO | WO 00/06747 A2 | 2/2000 |
| WO | WO 00/78985 A1 | 12/2000 |
| WO | WO 02/40690 A3 | 5/2002 |

OTHER PUBLICATIONS

Madison et al. (Microbiol and Mol boil. 1999, pp. 21-53).*

Rehm, Brend H.A., et al; "Matrix-assisted in vitro refolding of *Pseudomonas aeruginosa* class II polyhydroxyalkanoate synthase from inclusion bodies produced in recombinant *Escherichia coli*"; *Biochemical Society*; Aug. 15, 2001; 358 (Pt 1), pp. 263-268.

Qi, Q., et al; "In vitro synthesis of poly(3-hydroxydecanoate): purification and enzymatic characterization of type II polyhydroxyalkanoate synthases PhaC1 and PhaC2 from *Pseudomonas aeruginosa*"; *Appl. Microbiol Biotechnol*; Jul. 2000; 54(1): pp. 37-43.

Schubert, P. et al; "Molecular Analysis of the *Alcaligenes eutrophus* Poly(3-Hydroxybutyrate) Biosynthetic Operon: Identification of the N Terminus of Poly(3-Hydroxybutyrate) Synthase and Identification of the Promoter"; *Journal of Bacteriology*, vol. 173, No. 1; Jan. 1991, pp. 168-175.

Yamane, Tsuneo, et al; "Growth-Associated Production of Poly(3-Hydroxyvalerate) from *n*-Pentanol by a Methylotrophic Bacterium, *Paracoccus denitrificans*"; *Applied and Environmental Microbiology*; Feb. 1996; vol. 62, No. 2, pp. 380-384.

York, Gregory M., et al; "Accumulation of the PhaP Phasin of *Ralstonia eutropha* Is Dependent on Production of Polyhydroxybutyrate in Cells"; *Journal of Bacteriology*; Jul. 2001; vol. 183, No. 14; pp. 4217-4226.

York, Gregory M., et al; "The *Ralstonia eutropha* PhaR Protein Couples Synthesis of the PhaP Phasin to the Presence of Polyhydroxybutyrate in Cells and Promotes Polyhydroxybutyrate Production"; *Journal of Bacteriology*; Jan. 2002; vol. 184, No. 1; pp. 59-66.

McCool, Gabriel J., et al; Polyhydroxyalkanoate Inclusion Body-Associated Proteins and Coding Region in *Bacillus megaterium; Journal of Bacteriology*; Jan. 1999; vol. 181, No. 2; pp. 585-592.

McCool, Gabriel J., et al; "PhaC and PhaR Are Required for Polyhydroxyalkanoic Acid Synthase Activity in *Bacillus megaterium*"; *Journal of Bacteriology*; Jul. 2001; vol. 183, No. 14; pp. 4235-4243.

Kranz, Robert G., et al; "Polyhydroxyalkanoate Production in *Rhodobacter capsulatus*: Genes, Mutants, Expression, and Physiology"; *Applied and Environmental Microbiology*; Aug. 1997; vol. 63, No. 8; pp. 3003-3009.

Mittendorf, Volker et al; "Synthesis of medium-chain-length polyhydroxyalkanoates in *Arabidopsis thaliana* using intermediates of peroxisomal fatty acid β-oxidation"; *Proc. Natl. Acad. Sci.* USA; Nov. 1998; vol. 95; pp. 13397-13402.

Pieper-Furst, Ursula, et al; "Identification of the Region of a 14-Kilodalton Protein of *Rhodococcus ruber* That Is Responsible for the Binding of This Phasin to Polyhydroxyalkanoic Acid Granules"; *Journal of Bacteriology*; May 1995, vol. 177, No. 9; pp. 2513-2523.

Sim, S. J., et al; "PHA synthase activity controls the molecular weight and polydispersity of polyhydroxybutyrate in vivo"; *Nature Biotechnology*; (1997); vol. 15; pp. 63-67; XP002268360.

Steinbuchel, A., et al; "Diversity of bacterial polyhydroxyalkanoic acids"; *FEMS Microbiology Letters*; vol. 128, No. 3 (1995); pp. 219-228; SP000828495.

(Continued)

Primary Examiner—Tekchand Saidha
(74) Attorney, Agent, or Firm—Nixon & Vanderhye

(57) ABSTRACT

The invention relates to a method for producing biodegradable, functionalised polymer particles, and to the use of the same as medicament carriers.

22 Claims, 7 Drawing Sheets

OTHER PUBLICATIONS

Kreuter, J.; "Nanoparticulate systems for brain delivery of drugs"; *Advanced Drug Delivery Reviews*; vol. 47, No. 1 (2001); pp. 65-81; SP001119510.

Madison, L.L., et al; "Metabolic Engineering of Poly(3-Hydroxyalkanoates): From DNA to Plastic"; *Microbiology and MolecularBiology Reviews*; vol. 63, No. 1 (1999); pp. 21-53; XP000869647.

Steinbuchel, A., et al; "Bacterial and Other Biological Systems for Polyester Production"; *Trends in Biotechnology, Elsevier Publications*; vol. 16, No. 10 (1998); pp. 419-427; XP004145649.

Jun, S.S., et al; "PHA Synthase Activity Controls the Molecular Weight and Polydispersity of Polyhydroxybutyrate in Vivo"; *Nature Biotechnology*; vol. 15, No. 1 (1997); pp. 63-67; XP002268360.

Steinbuechel, A., et al; "Diversity of Bacterial PolyhydroxyAlkanoic Acids"; *FEMS Microbiology Letters*; vol. 128, No. 3 (1995); pp. 219-228; XP000828495.

Kreuter, J.; "Nanoparticulate Systems for Brain Delivery of Drugs"; *Advanced Drug Delivery Reviews*; vol. 47, No. 1 (2001); pp. 65-81; XP001119510.

Yuan et al., Archives of Biochemistry and Biophysics, vol. 394, No. 1, Oct. 1, 87-98 (2001).

Ueda, S., et al; "Molecular Analysis of the Poly(3-Hydroxyalkanoate) Synthase Gene from a Methylotrophic Bacterium, *Paracoccus denitrificans*"; *Journal of Bacteriology*; vol. 178, No. 3, pp. 774-779 (1996).

* cited by examiner

Key to Fig. 1
German
Polymer-Kern

English
Polymer core

Key to Fig. 3
German
Polymerpartikeldurchmesser [nm]
Arabinose-Induktor [µM]

English
Polymer particle diameter [nm]
Arabinose inducer [µM]

Key to Fig. 4
German
Anzahl der Partikel/Zelle
Arabinose-Induktor [µM]

English
Number of particles/cell
Arabinose inducer [µM]

| Key to Fig. 5 | |
|---|---|
| German | English |
| Polymerpartikeldurchmesser (nm) | Polymer particle diameter (nm) |
| Phasin/Polymer-Synthase (mol/mol) | Phasin/polymer synthase (mol/mol) |

| Key to Fig. 6 | |
|---|---|
| German | English |
| Polymerpartikeldurchmesser [nm] | Polymer particle diameter [nm] |
| Substrat/Polymer-Synthase [mol/mol] | Substrate/polymer synthase [mol/mol] |

SEQUENCE LISTING

```
<160> NUMBER OF SEQ ID NOS: 15

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
aaaggcccca tggtcctcac cccggaaca                              29

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
aaaggccgga tcctcagggc actaccttca tcg                         33

<210> SEQ ID NO 3
<211> LENGTH: 708
<212> TYPE: DNA
<213> ORGANISM: Artificial Sequence
<220> FEATURE:
<223> OTHER INFORMATION: Sequence contains phaP-coding DNA from R.
      eutropha
```

-continued

```
<400> SEQUENCE: 3
aaaggcccca tgatcctcac cccggaacaa gttgcagcag cgcaaaaggc caacctcgaa        60
acgctgttcg gcctgaccac caaggcgttt gaaggcgtcg aaaagctcgt cgagctgaac       120
ctgcaggtcg tcaagacttc gttcgcagaa ggcgttgaca acgccaagaa ggcgctgtcg       180
gccaaggacg cacaggaact gctggccatc caggccgcag ccgtgcagcc ggttgccgaa       240
aagaccctgg cctacacccg ccacctgtat gaaatcgctt cggaaaccca gagcgagttc       300
accaaggtag ccgaggctca actggccgaa ggctcgaaga acgtgcaagc gctggtcgag       360
aacctcgcca agaacgcccc ggccggttcg gaatcgaccg tggccatcgt gaagtcggcg       420
atctccgctg ccaacaacgc ctacgagtcg gtgcagaagg cgaccaagca agcggtcgaa       480
atcgctgaaa ccaacttcca ggctgcggct acggctgcca ccaaggctgc ccagcaagcc       540
agcgccacgg cccgtacggc cacggcaaag aagacgacgg ctgcctgata actgcctgcg       600
ttgaagatgg accggctgcg gccggtccgt tggcaaagca tatcgacgcc tggcgtttgc       660
ggtgtgtttt gccaacgatg aaggtagtgc cctgaggatc cggcctttt                   708

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
aaagggccat ggctggcaag aagaattccg agaa                                    34

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5 aaaggggggat cctcagatca gggtaccggt gcctgtctg                              39

<210> SEQ ID NO 6
<211> LENGTH: 793
<212> TYPE: DNA
<213> ORGANISM: Artificial Sequence
<220> FEATURE:
<223> OTHER INFORMATION: Sequence contains phaF-coding DNA from P.
      oleovorans

<400> SEQUENCE: 6
aaagggccat ggctggcaag aagaattccg agaaagaagg cagctcctgg gtcggcggga        60
tcgagaagta ctcccgcaag atctggctgg cggggcttgg tatctattcg aagatcgacc       120
aggacggccc gaagctgttc gactcgctgg taaaggatgg cgagaaggcc gagaaacagg       180
cgaagaagac cgcagaagat gttgctgaaa ctgccaagtc gtcgaccact tcgcgtgtgt       240
cgggcgtgaa ggaccgtgcg ctaggcaagt ggagcgaact cgaagaggcc ttcgacaagc       300
gcctgaacag tgccatctcg cgccttggcg tgccgagccg caacgagatc aaggccctgc       360
accagcaggt ggacagcctg accaagcaga tcgagaaact caccggcgct tcggttaccc       420
cgatttcgtc gcgcactgca gccaaaccgg ctgcagcaa ggcggcgcc aagccactgg        480 ccaagacggc agcggccaag cctgcggcaa aaccgcggc agccaagccg gcagccaagg       540
```

-continued

```
ccgcagcggc taaacctgct gccaagactg cggcggccaa gcctgcggcg aaaccggcag        600
cggccaaacc ggctgtggcg aagaagcctg cagtgaagaa agcaccggcc aagccggcag        660
ccgccaagcc ggcagctcca gcggccagcg ccgctccggc cgctagcgca gttcggcgcc        720
cactgcggct ccggccagca acccgccttc ggcacagaca ggcaccggta ccctgatctg        780
aggatccccc ttt                                                          793
```

<210> SEQ ID NO 7
<211> LENGTH: 54
<212> TYPE: DNA
<213> ORGANISM: Artificial Sequence
<220> FEATURE:
<223> OTHER INFORMATION: Primer

<400> SEQUENCE: 7

```
gggctctaga aataaggaga tatacatatg tgttgtaaga acaataacga gctt              54
```

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8

```
aaacgcggat cctttcatc gttcatgca                                           29
```

<210> SEQ ID NO 9
<211> LENGTH: 1722
<212> TYPE: DNA
<213> ORGANISM: Artificial Sequence
<220> FEATURE:
<223> OTHER INFORMATION: Sequence contains the DNA coding for PhaC1 from
      P. aeruginosa

<400> SEQUENCE: 9

```
gggctctaga aataaggaga tatacatatg tgttgtaaga acaataacga gcttcccaag        60
caagccgcgg aaaacacgct gaacctgaat ccggtgatcg gcatccgggg caaggacctg       120
ctcacctccg cgcgcatggt cctgctccag gcggtgcgcc agccgctgca cagcgccagg       180
cacgtggcgc atttcagcct ggagctgaag aacgtcctgc tcggccagtc ggagctacgc       240
ccaggcgatg acgaccgacg cttttccgat ccggcctgga gccagaatcc actgtacaag       300
cgctacatgc agacctacct ggcctggcgc aaggagctgc acagctggat cagccacagc       360
gacctgtcgc cgcaggacat cagtcgtggc cagttcgtca tcaacctgct gaccgaggcg       420
atgtcgccga ccaacagcct gagcaacccg cggcggtca agcgcttctt cgagaccggc       480
ggcaagagcc tgctggacgg cctcggccac ctggccaagg acctggtgaa caacggcggg       540
atgccgagcc aggtggacat ggacgccttc gaggtgggca gaacctggc caccaccgag       600 ggcgccgtgg tgttccgcaa cgacgtgctg aactgatcc agtaccggcc gatcaccgag       660
tcggtgcacg aacgcccgct gctggtggtg ccgccgcaga tcaacaagtt ctacgtcttc       720
gacctgtcgc cggacaagag cctggcgcgc ttctgcctgc gcaacggcgt gcagaccttc       780
atcgtcagtt ggcgcaaccc gaccaagtcg cagcgcgaat ggggcctgac cacctatatc       840
gaggcgctca aggaggccat cgaggtagtc ctgtcgatca ccggcagcaa ggacctcaac       900
ctcctcggcg cctgctccgg cgggatcacc accgcgaccc tggtcggcca ctacgtggcc       960
agcggcgaga agaaggtcaa cgccttcacc caactggtca gcgtgctcga cttcgaactg      1020
```

```
aatacccagg tcgcgctgtt cgccgacgag aagactctgg aggccgccaa gcgtcgttcc    1080
taccagtccg gcgtgctgga gggcaaggac atggccaagg tgttcgcctg gatgcgcccc    1140
aacgacctga tctggaacta ctgggtcaac aactacctgc tcggcaacca gccgccggcg    1200
ttcgacatcc tctactggaa caacgacacc acgcgcctgc ccgccgcgct gcacggcgag    1260
ttcgtcgaac tgttcaagag caacccgctg aaccgccccg gcgccctgga ggtctccggc    1320
acgcccatcg acctgaagca ggtgacttgc gacttctact gtgtcgccgg tctgaacgac    1380
cacatcaccc cctgggagtc gtgctacaag tcggccaggc tgctgggtgg caagtgcgag    1440
ttcatcctct ccaacagcgg tcacatccag agcatcctca acccaccggg caaccccaag    1500
gcacgcttca tgaccaatcc ggaactgccc gccgagccca aggcctggct ggaacaggcc    1560
ggcaagcacg ccgactcgtg gtggttgcac tggcagcaat ggctggccga acgctccggc    1620
aagacccgca aggcgcccgc cagcctgggc aacaagacct atccggccgg cgaagccgcg    1680
cccggaacct acgtgcatga acgatgaaaa ggatccgcgt tt                      1722
```

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10

```
tatgactagt gattataaag atgatgatga taaaca                              36
```

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11

```
tatgtttatc atcatcatct ttataatcac tagtca                              36
```

<210> SEQ ID NO 12
<211> LENGTH: 1716
<212> TYPE: DNA
<213> ORGANISM: Artificial Sequence
<220> FEATURE:
<223> OTHER INFORMATION: Sequence contains the DNA coding for PhaC1 from
      P. aeruginosa and the DNA coding for a FLAG epitope

<400> SEQUENCE: 12

```
atgactagtg attataaaga tgatgatgat aaacatatga gtcagaagaa caataacgag     60
cttcccaagc aagccgcgga aaacacgctg aacctgaatc cggtgatcgg catccggggc    120
aaggacctgc tcacctccgc gcgcatggtc ctgctccagg cggtgcgcca gccgctgcac    180
agcgccaggc acgtggcgca tttcagcctg agctgaaga acgtcctgct cggccagtcg    240
gagctacgcc caggcgatga cgaccgacgc ttttccgatc cggcctggag ccagaatcca    300
ctgtacaagc gctacatgca gacctacctg gcctggcgca aggagctgca cagctggatc    360
agccacagcg acctgtcgcc gcaggacatc agtcgtggcc agttcgtcat caacctgctg    420
accgaggcga tgtcgccgac caacagcctg agcaacccgg cggcggtcaa gcgcttcttc    480
gagaccggcg gcaagagcct gctgacggc ctcggccacc tggccaagga cctggtgaac    540
aacggcggga tgccgagcca ggtggacatg gacgccttcg aggtgggcaa gaacctggcc    600
```

```
accaccgagg gcgccgtggt gttccgcaac gacgtgctgg aactgatcca gtaccggccg      660
atcaccgagt cggtgcacga acgcccgctg ctggtggtgc cgccgcagat caacaagttc      720
tacgtcttcg acctgtcgcc ggacaagagc ctggcgcgct tctgcctgcg caacggcgtg      780
cagaccttca tcgtcagttg gcgcaacccg accaagtcgc agcgcgaatg gggcctgacc      840
acctatatcg aggcgctcaa ggaggccatc gaggtagtcc tgtcgatcac cggcagcaag      900
gacctcaacc tcctcggcgc ctgctccggc gggatcacca ccgcgaccct ggtcggccac      960
tacgtggcca gcggcgagaa gaaggtcaac gccttcaccc aactggtcag cgtgctcgac     1020
ttcgaactga atacccaggt cgcgctgttc gccgacgaga agactctgga ggccgccaag     1080
cgtcgttcct accagtccgg cgtgctggag ggcaaggaca tggccaaggt gttcgcctgg     1140
atgcgcccca cgacctgat  ctggaactac tgggtcaaca actacctgct cggcaaccag     1200
ccgccggcgt cgacatcct  ctactggaac aacgacacca cgcgcctgcc cgccgcgctg     1260
cacggcgagt cgtcgaact  gttcaagagc aacccgctga accgcccgg  cgccctggag     1320 gtctccggca cgcccatcga cctgaagcag gtgacttgcg acttctactg tgtcgccggt     1380
ctgaacgacc acatcacccc ctgggagtcg tgctacaagt cggccaggct gctggggtggc    1440 aagtgcgagt tcatcctctc caacagcggt cacatccaga gcatcctcaa cccaccgggc     1500 aacccccaagg cacgcttcat gaccaatccg gaactgcccg ccgagcccaa ggcctggctg    1560
gaacaggccg gcaagcacgc cgactcgtgg tggttgcact ggcagcaatg gctggccgaa     1620
cgctccggca agacccgcaa ggcgcccgcc agcctgggca caagaccta  tccggccggc     1680 gaagccgcgc ccggaaccta cgtgcatgaa cgatga                               1716

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
ggactagtat gaccatgatt acggattcac tggc                                   34

<210> SEQ ID NO 14
<211> LENGTH: 41
<212> TYPE: DNA
<213> ORGANISM: Artificial Sequence
<220> FEATURE:
<223> OTHER INFORMATION: Primer

<400> SEQUENCE: 14
ccactagttt tttgacacca gaccaactgg taatggtagc g                           41

<210> SEQ ID NO 15
<211> LENGTH: 3088
<212> TYPE: DNA
<213> ORGANISM: Artificial Sequence
<220> FEATURE:
<223> OTHER INFORMATION: Sequence contains the lac-Z gene from E. coli

<400> SEQUENCE: 15
ggactagtat gaccatgatt acggattcac tggccgtcgt tttacaacgt cgtgactggg       60
aaaaccctgg cgttacccaa cttaatcgcc ttgcagcaca tccccctttc gccagctggc      120
gtaatagcga agaggcccgc accgatcgcc cttcccaaca gttgcgcagc ctgaatggcg      180
aatggcgctt tgcctggttt ccggcaccag aagcggtgcc ggaaagctgg ctggagtgcg      240
```

-continued

```
atcttcctga ggccgatact gtcgtcgtcc cctcaaactg gcagatgcac ggttacgatg    300
cgcccatcta caccaacgtg acctatccca ttacggtcaa tccgccgttt gttcccacgg    360
agaatccgac gggttgttac tcgctcacat ttaatgttga tgaaagctgg ctacaggaag    420
gccagacgcg aattattttt gatggcgtta actcggcgtt tcatctgtgg tgcaacgggc    480
gctgggtcgg ttacggccag acagtcgtt tgccgtctga atttgacctg agcgcatttt    540
tacgcgccgg agaaaaccgc tcgcggtga tggtgctgcg ctggagtgac ggcagttatc    600
tggaagatca ggtatatgtg cggatgagcg gcattttccg tgacgtctcg ttgctgcata    660
aaccgactac acaaatcagc gatttccatg ttgccactcg ctttaatgat gatttcagcc    720
gcgctgtact ggaggctgaa gttcagatgt gcggcgagtt gcgtgactac ctacgggtaa    780
cagtttcttt atggcagggt gaaacgcagg tcgccagcgg caccgcgcct tcggcggtg    840
aaattatcga tgagcgtggt ggttatgccg atcgcgtcac actacgtctg aacgtcgaaa    900
acccgaaact gtggagcgcc gaaatcccga atctctatcg tgcggtggtt gaactgcaca    960
ccgccgacgg cacgctgatt gaagcagaag cctgcgatgt cggtttccgc gaggtgcgga   1020
ttgaaaatgg tctgctgctg ctgaacggca agccgttgct gattcgaggc gttaaccgtc   1080
acgagcatca tcctctgcat ggtcaggtca tggatgagca gacgatggtg caggatatcc   1140
tgctgatgaa gcagaacaac tttaacgccg tgcgctgttc gcattatccg aaccatccgc   1200
tgtggtacac gctgtgcgac cgctacggcc tgtatgtggt ggatgaagcc aatattgaaa   1260
cccacggcat ggtgccaatg aatcgtctga ccgatgatcc gcgctggcta ccggcgatga   1320
gcgaacgcgt aacgcgaatg gtgcagcgcg atcgtaatca cccgagtgtg atcatctggt   1380
cgctggggaa tgaatcaggc cacggcgcta atcacgacgc gctgtatcgc tggatcaaat   1440
ctgtcgatcc ttcccgcccg gtgcagtatg aaggcggcgg agccgacacc acggccaccg   1500
atattatttg cccgatgtac gcgcgcgtgg atgaagacca gcccttcccg gctgtgccga   1560
aatggtccat caaaaaatgg ctttcgctac ctggagagac gcgcccgctg atcctttgcg   1620
aatacgccca cgcgatgggt aacagtcttg gcggtttcgc taaatactgg caggcgtttc   1680
gtcagtatcc ccgtttacag ggcggcttcg tctgggactg ggtggatcag tcgctgatta   1740
aatatgatga aaacggcaac ccgtggtcgg cttacggcgg tgattttggc gatacgccga   1800
acgatcgcca gttctgtatg aacggtctgg tctttgccga ccgcacgccg catccagcgc   1860
tgacggaagc aaaacaccag cagcagttttt tccagttccg tttatccggg caaaccatcg   1920
aagtgaccag cgaatacctg ttccgtcata gcgataacga gctcctgcac tggatggtgg   1980
cgctggatgg taagccgctg gcaagcggtg aagtgcctct ggatgtcgct ccacaaggta   2040
aacagttgat tgaactgcct gaactaccgc agccggagag cgccgggcaa ctctggctca   2100
cagtacgcgt agtgcaaccg aacgcgaccg catggtcaga agcccggcac atcagcgcct   2160
ggcagcagtg gcgtctggcg gaaaacctca gtgtgacgct ccccgccgcg tcccacgcca   2220
tcccgcatct gaccaccagc gaaatggatt tttgcatcga gctgggtaat aagcgttggc   2280
aatttaaccg ccagtcaggc tttctttcac agatgtggat tggcgataaa aaacaactgc   2340
tgacgccgct cgcgcgatcag ttcacccgtg caccgctgga taacgacatt ggcgtaagtg   2400
aagcgacccg cattgaccct aacgcctggg tcgaacgctg gaaggcggcg ggccattacc   2460
aggccgaagc agcgttgttg cagtgcacgg cagatacact tgctgatgcg gtgctgatta   2520
cgaccgctca cgcgtggcag catcagggga aaaccttatt tatcagccgg aaaacctacc   2580
```

-continued

```
ggattgatgg tagtggtcaa atggcgatta ccgttgatgt tgaagtggcg agcgatacac    2640
cgcatccggc gcggattggc ctgaactgcc agctggcgca ggtagcagag cgggtaaact    2700
ggctcggatt agggccgcaa gaaaactatc ccgaccgcct tactgccgcc tgttttgacc    2760
gctgggatct gccattgtca gacatgtata ccccgtacgt cttcccgagc gaaaacggtc    2820
tgcgctgcgg gacgcgcgaa ttgaattatg gcccacacca gtggcgcggc gacttccagt    2880
tcaacatcag ccgctacagt caacagcaac tgatggaaac cagccatcgc catctgctgc    2940
acgcggaaga aggcacatgg ctgaatatcg acggtttcca tatggggatt ggtggcgacg    3000
actcctggag cccgtcagta tcggcggaat tccagctgag cgccggtcgc taccattacc    3060
agttggtctg gtgtcaaaaa actagtgg                                      3088
```

PROCESS FOR THE PRODUCTION OF BIODEGRADABLE, FUNCTIONALISED POLYMER PARTICLES, AND USE THEREOF AS PHARMACEUTICAL SUPPORTS

This application is the U.S. National Phase of International Application PCT/DE03/002799 filed 22 Aug. 2003, which designated the U.S. PCT/DE03/002799 claims priority to German Application No. 102 40 035.0 filed 30 Aug. 2002. The entire content of these applications are incorporated herein by reference.

The present invention relates to a process for the production of biodegradable, functionalised polymer particles and to the use thereof as pharmaceutical supports.

PRIOR ART

The effectiveness of many active ingredients depends upon whether they are transported exactly to the desired target site in the body as the active ingredients used are frequently able to exert their full action only at a specific location and are ineffective at other locations or even have negative effects there. The latter particularly applies when combating cancerous conditions and in particular cancerous conditions occurring in the central nervous system (CNS).

One good example of the difficulties which may occur on transport of active ingredients in the animal body is the blood-brain barrier (BBB). Active ingredients destined for the CNS must first cross this barrier. This network of blood vessels and cells protects the CNS and prevents non-water-soluble substances from entering the CNS. Fat-soluble substances can straightforwardly pass through this barrier by simple diffusion. Active and passive transport systems are, however, necessary for the transport of polar substances and ions. However, since, for example, more than 98% of all newly discovered medicines destined for the CNS are not water-soluble, they cannot cross the BBB and thus cannot reach their target site.

This example is intended to illustrate the difficulties which may occur during transport of active ingredients in the animal organism. In the case of the BBB, for example, it has been attempted to make it more permeable to active ingredients by modifying the membrane's permeability. Permeability of the BBB to active ingredients may, for example, be achieved by artificially increasing osmotic pressure or by administering bradykinin analogues. Sanovich et al. (Sanovich, E. et al., Brain Res. 1995, Vol. 705(1-2), pp. 125-135) and others have, for example, demonstrated increased permeability of the BBB to lanthanum by simultaneous administration with the bradykinin analogue RMP-7. One fundamental disadvantage of opening the BBB by one of the above-stated mechanisms is that permeability to all substances, which thus also includes toxic substances which can damage the target cells in the CNS, is consequently increased.

Another possibility is to modify the active ingredient chemically in such a manner that it becomes more lipophilic and may thus also more readily pass through the BBB, as has for example been demonstrated for chlorambucil derivatives (Greig, N. H. et al., Cancer Chemother. Pharmacol. 1990, Vol. 25(5), pp. 320-325).

An alternative to both the above-stated systems is to use nano- or microparticles, the use of which does not entail modifying either the permeability of the membrane or the active ingredient. Kreuter (Kreuter, J. J. Anat. 1996, Vol. 189(3), pp. 503-505) demonstrates that the polymer particles used for this purpose are substantially produced by chemical processes, such as emulsion polymerisation, interfacial polymerisation, desolvation, evaporation and solvent precipitation.

According to DE 197 45 950 A1, polymer particles prepared from the most varied substances (polymers (in this case: polybutyl cyanoacrylate), solid or liquid lipids, o/w emulsions, w/o/w emulsions or phospholipid vesicles), to which the pharmaceutical substances are attached, are used to transport these substances into the CNS.

Another critical factor in the transport of nano- and microparticles through a membrane, and in particular the membranes of the BBB, is the size of the polymer particles. Previous research results show that polymer particles up to a size of 270 nm are capable of getting through the BBB (Lockman, P. R. et al., Drug Develop. Indust. Pharmacy 2002, Vol. 28(1), pp. 1-12).

It is thus important for the polymer particles used to be of a specific size. According to Lockmann (Lockman, P. R. et al., Drug Develop. Indust. Pharmacy 2002, Vol. 28(1), pp. 1-12), the size of the polymer particles produced by the above processes is generally determined by photon correlation spectroscopy. This method, which is based on Brownian motion, measures the polymer particles with a laser beam, the time dependency of light variation being used to determine particle size. However, this analytical method for the subsequent determination of the size of the polymer particles produced is very time-consuming and costly.

The object of the present invention is accordingly to provide a rapidly usable, low cost transport system for biologically active substances which permits effective and reliable transport of active ingredients in the animal organism.

For the purposes of the present invention, "biologically active substance" is any substance capable of initiating a biological response on the part of the organism. These substances comprise not only enzymes and abzymes, which catalyse a specific reaction in the organism, and proteins, such as for example antibodies, which bring about an indirect response of the organism to the presence of this substance in the organism, but also inorganic and organic molecules which are non-biological in origin, i.e. are not formed by a naturally occurring organism, but are instead produced artificially. Most pharmaceutical active ingredients also belong to the latter group. Depending on their nature, the biologically active substances may also be suitable for binding further biologically active substances.

A process for the production of biodegradable polymer particles is provided in order to achieve the above-stated object. This process involves introducing at least one inducible gene into a microorganism, wherein the gene codes for a protein which controls the size of the polymer particles, and culturing the microorganism with induction of the above-stated, at least one inducible gene in a culture medium under conditions which are suitable for the production of the biodegradable polymer particles by the microorganism. By means of this process, it is possible to produce biocompatible, biodegradable polymer particles which are suitable for transporting biologically active substances and wherein, by controlling the size of the polymer particles formed, said particles may be produced as required in the desired size. Due to the controlled production of polymer particles of a specific size, the yield of polymer particles of the desired size is increased, so increasing the efficiency of the process and simultaneously helping to reduce costs. Moreover, polymer particles may be produced by the process according to the invention which meet the above-stated particle size requirement for transport through the BBB. Thanks to this process it is above all possible to produce polymer particles which are smaller than the polymer particles of this kind naturally produced by microorganisms. The average size of the polymer particles naturally produced by microorganisms is 300 to 500 nm (Wieczorek, R. et al, J. Bacteriol. 1997, Vol. 177(9), pp. 2425-2435), while the process according to the invention makes it possible to control production of the polymer particles in such a manner that they are considerably smaller than this average value.

The particle size-determining gene is here induced by an upstream inducible promoter, such as for example a BAD promoter, which is induced by arabinose. The microorganisms used for this purpose have no gene for controlling the size of the polymer particles or this gene is inactivated and replaced by the at least one inducible gene described in the process according to the invention, which gene codes for a protein which controls the size of the polymer particles. This gene is here introduced into the cell by means of a vector which is described in greater detail in the experimental section of this description. As a consequence, it is for the first time possible to produce biocompatible, biodegradable polymer particles of a defined size in a microbial process.

These polymer particles are deposited as cytoplasmic inclusions in the cell. The core of these polymer particles consists of polyhydroxyalkyl carboxylates, in particular polyhydroxy alkanoates, and is enclosed by a shell membrane consisting of proteins and phospholipids. The shell membrane consists of lipids and proteins embedded therein. The polyhydroxyalkyl carboxylates, which form the core of these polymer particles, have melting points of 50° C. to 176° C., a crystallinity of 30% to 70% and elongation at break values of 5% to 300%.

In order also to be able to use this advantageous process in microorganisms which are more suited to biotechnological cultivation (for example certain forms of *E. coli*, which are classified as GRAS organisms) but, due to their genetic makeup, are unable to form the above-stated polymer particles, at least one further gene which codes for a protein involved in the formation of the polymer particles is introduced as well as the at least one inducible gene which codes for a protein which controls the size of the polymer particles. Any protein capable of influencing the metabolism leading to formation of the polymer particles and thus the composition of the polymer particles formed may be considered. The at least one further gene which codes for a protein involved in the formation of the polymer particles is here selected such that it codes for a thiolase, a reductase or a polymer synthase. A polymer synthase is taken to be any protein which is capable of catalysing the final step for formation of a polymer. Apart from the polymer synthases described in the present invention, formation of a polymer may, for example, also be undertaken by a lipase. The at least one further gene which codes for a protein involved in the formation of the polymer particles is preferably selected such that it codes for phaA thiolase, phaB ketoacyl reductase or phaC synthase from *Ralstonia eutropha*. Due to the introduction of these additional genes, the cell is enabled to produce proteins which allow it to form the polymer particles. Purposeful selection of the at least one further gene which codes for a protein involved in the formation of the polymer particles also makes it possible to influence the subsequent composition of the polymer particles. Genes which code for proteins involved in the metabolic pathway towards formation of the polymer particles may have different substrate specificities, form different reaction products or block branches in the metabolic pathway in order to exert a purposeful influence on the substrates and molecules involved in the formation of the polymer particles.

In order to allow production of the polymer particles in microorganisms, such as the mutants of the genus *E. coli* described in Example 4, which have a modified fatty acid metabolism, all that is required, apart from the at least one inducible gene which codes for a protein which controls the size of the polymer particles, is the polymer synthase. Depending on which organism is used, further genes may be introduced into the cell in order to enable production of the polymer particles under the stated conditions. If a cell does not contain all the genes required for formation of the polymer particles, production of the polymer particles may nevertheless proceed if the intermediates produced by the missing proteins are supplied to the cell via the nutrient medium. At least one polymer synthase is, however, always required for formation of the polymer particles.

The properties of the polymer particles may be influenced by controlling the composition thereof. By influencing their properties, it is, for example, possible to influence the rate of biodegradability of the polymer particles. Apart from the above-stated possibility of purposefully selecting the further genes introduced into the cell which code for a protein involved in the formation of the polymer particles, it is particularly preferred for the purposes of influencing the composition of the polymer particles formed in vivo to introduce into the cell at least one additional gene which codes for a thiolase and/or a polymer synthase. The differing substrate specificity of the thiolases and polymer synthases results in different intermediate and final products and thus in a different composition of the formed polymer core of the particle.

The principle underlying the production of these polymer particles is illustrated by way of example in FIG. 2. Activated precursors for biosynthesis of the polymers may in principle be derived from the central metabolites acetyl CoA or from intermediates of the primary metabolic pathways the citrate cycle, fatty acid β oxidation and de novo fatty acid biosynthesis, and from amino acid metabolism. If fatty acids are used as the carbon source, intermediates (acyl CoA, in particular 3-hydroxyacyl CoA), which serve as activated precursors for PHA biosynthesis, are produced by fatty acid β oxidation.

Particle size is controlled in that the at least one inducible gene which codes for a protein which controls the size of the polymer particles is derived from the family of phasin-like proteins and is preferably selected from the group comprising the phasin gene phaP from *Ralstonia eutropha* and the phasin gene phaF from *Pseudomonas oleovorans*. Phasins are amphiphilic proteins with a molecular weight of 14 to 28 kDa which bind tightly to the hydrophobic surface of the polymer particles.

Polymer particles with a different composition of the polymers forming them exhibit different mechanical properties and release biologically active substances, in particular pharmaceutical active ingredients, at different rates. For example, polymer particles composed of C6-C14 3-hydroxy fatty acids exhibit a higher rate of polymer degradation due to the low crystallinity of the polymer. An increase in the molar ratio of polymer constituents with relatively large side chains on the polymer backbone usually reduces crystallinity and results in more pronounced elastomeric properties. By controlling polymer composition in accordance with the process described in the invention, it is accordingly possible to influence the biodegradability of the polymer particles and thus also the release rate for biologically active substances, in particular pharmaceutical active ingredients.

At least one fatty acid with functional side groups is preferably introduced into the culture medium as a substrate for the formation of the polymer particles, with at least one hydroxy fatty acid and/or at least one mercapto fatty acid and/or at least one β-amino fatty acid particularly preferably being introduced. "Fatty acids with functional side groups" should be taken to mean saturated or unsaturated fatty acids. These also include fatty acids containing functional side groups which are selected from the group comprising methyl groups, alkyl groups, hydroxyl groups, phenyl groups, sulfhydryl groups, primary, secondary and tertiary amino groups, aldehyde groups, keto groups, ether groups, carboxyl groups, O-ester groups, thioester groups, carboxylic acid amide groups, hemiacetal groups, acetal groups, phosphate monoester groups and phosphate diester groups.

Use of the substrates is determined by the desired composition and the desired properties of the polymer particles, which are influenced both genetically by the use of different genes which code for proteins with different substrate specificity and by the additives, substrates and reaction conditions present in the culture medium which are used.

In order to achieve still more accurate control of the size of the polymer particles formed, the substrate is added to the culture medium in a quantity such that it is sufficient to ensure control of the size of the polymer particles. This yields an additional possibility for exerting still more effective control over particle size.

The microorganism used to form the polymer particles in the process according to the invention is selected from the genera comprising *Ralstonia, Acaligenes, Pseudomonas* and *Halobiforma*. The microorganism used is preferably selected from the group comprising *Ralstonia eutropha, Alcaligenes latus, Escherichia coli, Pseudomonas fragi, Pseudomonas putida, Pseudomonas oleovorans, Pseudomonas aeruginosa, Pseudomonas fluorescens*, and *Halobiforma haloterrestris*. This group comprises both microorganisms which are naturally capable of producing biocompatible, biodegradable polymer particles and microorganisms, such as for example *E. coli*, which, due to their genetic makeup, are not capable of so doing. The genes required to enable the latter-stated microorganisms to produce the polymer particles are introduced using the process according to the invention. In principle, any culturable microorganism may be used for the production of polymer particles by means of the above-described process, even if the microorganism cannot produce the substrates required to form the polymer particles due to a different metabolism. In such cases, the necessary substrates are added to the culture medium and are then converted into polymer particles by the proteins which have been expressed by the genes which have been introduced into the cell.

In order to obtain the polymer particles from the cells, the cultured microorganisms are disrupted in per se known manner and the polymer particles are then separated from the cell debris. The size range of the polymer particles obtained in this manner may be narrowed still further using standard methods, such as for example exclusion chromatography or density gradient centrifugation, to select the polymer particles of the desired size.

The shell membrane consisting of proteins and lipids of the polymer particles produced according to the invention may also be modified in order to impart to the particles properties which are more favourable to the transport of the active ingredients in the animal body. To this end, a lipid layer located on the surface of the polymer particles is separated from the polymer particles obtained in the process according to the invention and is replaced by a lipid layer of a different composition.

When replacing the lipid layer by a lipid layer of a different composition, the properties of the new lipid layer which are of significance are those having an influence on the transport of the polymer particles through a biological membrane. If the lipid layer of the shell membrane matches the lipid layer of the target membrane, better particle uptake may be observed (Fernart, L. et al., J. Pharmacol. Exp. Ther. 1999, Vol. 291(3), pp. 1017-1022). The lipid layer of the polymer particles may accordingly be removed and be replaced by a lipid layer of a different composition. This is preferably achieved by acetone extraction or phospholipases or non-denaturing detergents are used. A mixture of the appropriate amphiphilic molecules is then added to the now virtually lipid-free polymer particles in order to obtain a lipid layer of the desired composition. The new lipid layer here preferably consists of a mixture of amphiphilic molecules which are selected from the group comprising phospholipids and ether lipids.

In addition to the lipids, it is also possible to remove the proteins located on the surface of the polymer particles, with the exception of polymer synthase, by using the above-stated detergents and to replace them with functionalised proteins. Naked polymer particles may in this manner be prepared for numerous modification possibilities which are described in greater detail below. Polymer particles obtained from the microorganism *H. haloterrestris* are particularly suitable for this type of modification.

Depending on the subsequent application of the polymer particles, particle size is controlled by the at least one inducible gene in such a manner that the polymer particles formed have a diameter of 10 nm to 3 μm, preferably of 1 nm to 900 nm and particularly preferably of 10 nm to 100 nm. In one particular embodiment of the present invention, this size control may also be achieved by controlling the availability of a substrate in the culture medium or by combining the two mechanisms.

For the purposes of functionalising the polymer particles produced using the process according to the invention, it is necessary for the at least one inducible gene introduced in the process which codes for a protein which controls the size of the polymer particles to comprise a polymer particle binding domain and at least one binding domain, wherein the at least one binding domain is capable of binding a biologically active substance and/or a coupling reagent. It is likewise particularly preferred for the at least one further gene which codes for a protein involved in the formation of the polymer particles to comprise a polymer particle binding domain and at least one binding domain, wherein the at least one binding domain is capable of binding a biologically active substance and/or a coupling reagent.

A "binding domain" designates that part of the protein which is obtained by genetic modification of the at least one inducible gene previously introduced into the cell and/or of the at least one further gene which codes for a protein involved in the formation of the polymer particles. The binding domain capable of binding the biologically active substances and/or a coupling reagent is selected from the group comprising oligopeptides, enzymes, abzymes and non-catalytic proteins. This group particularly preferably comprises FLAG epitopes or at least one cysteine. These groups are also designated functional proteins in the experimental section. The coding sequence for the members stated in this group is inserted in the coding sequence of the at least one inducible gene previously introduced into the cell and/or of the at least one further gene which codes for a protein involved in the formation of the polymer particles. In this manner, proteins are produced which are not only involved in the formation of or the control of the formation of the polymer particles, but, thanks to their binding domain obtained by genetic modification, are also capable of binding biologically active substances and/or coupling reagents. The binding domain may also be obtained after production of the polymer particles by chemically modifying the proteins located on the surface with coupling reagents (c.f. Example 8).

A "coupling reagent" for this purpose is an inorganic or organic compound which is suitable for binding to itself a biologically active substance or further coupling reagents on one side and the binding domain on the other side.

This structure makes it possible to produce multifunctional polymer particles which are suitable for transporting biologically active substances. The "polymer particle binding domain" preferably consists of part of a protein which enables it to bind to the hydrophobic surface of the polymer particles. The polymer particle domain which comprises part of a protein bound on the surface of the polymer particle is here selected from the group of proteins which comprises a polymer depolymerase, a polymer regulator, a polymer synthase and a particle size-determining protein. These proteins preferably originate from microorganisms which are capable of forming polymer particles, in particular those from the genera *Ralstonia, Alcaligenes* and *Pseudomonas*. The particle size-controlling protein is here preferably derived from the family of phasin-like proteins and the phasin from *R. eutropha* and *P. oleovorans* is still more preferably used.

A "polymer regulator" for the purposes of the invention is a protein which regulates the transcription of the genes phaA, phaB and phaC involved in the formation of the polymer particles. It is withdrawn from transcription regulation by binding to the particle surface. One example of such a regulator is the phasin repressor (phaR) from *R. eutropha*, which binds to the promoter of a phasin-like gene, the expression product of which regulates the size of polymer particles formed, and prevents the gene from being read. Because the phasin repressor is bound on the surface of the polymer particles formed, this site on the promoter is released and transcription of the underlying gene can begin.

The idea of using the binding domain of a polymer synthase for binding coupling reagents and/or biologically active substances arises from the elevated stability of the bond between the polymer particle binding domain of this protein and the core of the polymer particle. The inventor has surprisingly discovered that this bond cannot be detached from the core of the biodegradable polymer particle either by denaturing reagents, such as for example. sodium dodecyl sulfate (SDS), urea, guanidium hydrochloride or dithiothreitol, nor by using acidic conditions. The polymer synthase derived from *R. eutropha, P. oleovorans, P. putida* or *P. aeruginosa* is preferably used for this purpose.

It is here a particular advantage of the process according to the invention that the genetic engineering modification of the proteins binding to the surface of the polymer particles does not affect the functionality of the proteins involved in the formation of the polymer particles. For example, the functionality of the polymer synthase is retained if a protein is fused with the N-terminal end thereof, resulting in the production of a binding domain for binding biologically active substances and/or coupling reagents. Should the functionality of a protein nevertheless be impaired by the fusion, this shortcoming may be offset by the presence of a further gene which codes for a protein which performs the same function and is present in an active state.

In this manner, it is possible to ensure a stable bond of the biologically active substances and/or coupling reagents bound to the polymer particles via the binding domain of the proteins, in particular polymer synthase.

During genetic engineering modification of the genes which code for proteins which, once expressed, bind to the particle surface, it is also possible to introduce genes with different modifications into the cell. Once these proteins with their different binding domains have been expressed and the polymer particles have been formed, it is possible in this manner to use the different binding domains to multifunctionalise the particle surface. This process enables straightforward and efficient mass production of functionalised polymer particles.

Coupling reagents are used for the subsequent functionalisation of the proteins bound on the surface of the polymer particles, these coupling reagents preferably being selected from the group comprising bis(2-oxo-3-oxazolydinyl)phosphonic chloride (BOP-Cl), bromotrispyrrolidinophosphonium hexafluorophosphate (PyBroP), benzotriazol-1-yl-oxytrispyrrolidinophosphonium hexafluorophosphate (PyBOP), n-hydroxysuccinimide biotin, 2-(1H-benzotriazol-1-yl)-1,1,3,3-tetramethyluronium hexafluorophosphate (HBTU), dicyclohexylcarbodiimide, disuccinimidyl carbonate, 1-(3-dimethylaminopropyl)-3-ethylcarbodiimide (EDC), bis(2-oxo-3-oxazolydinyl)phosphine, diisopropylcarbodiimide (DIPC), 2-(1H-benzotrioxazolyl)-1,1,3,3-tetramethyluronium tetrafluoroborate (TBTU), 2-(5-norbornene-2,3-dicarboxyimido)-1,1,3,3-tetramethyluronium tetrafluoroborate (TNTU), para-nitrophenylchloroformate, and O-(n-succinimidyl)-1,1,3,3-tetramethyluronium tetrafluoroborate (TSTU).

The biologically active substances used are preferably pesticides, herbicides, pharmaceutically active substances and proteins.

The pharmaceutically active substances are selected from the group comprising dideoxyinosine, floxuridine, 6-mercaptopurine, doxorubicin, daunorubicin, 1-darubicin, cisplatin, methotrexate, taxol, antibiotics, anticoagulants, germicides, antiarrhythmic agents and active ingredient precursors and derivatives of the listed groups of active ingredients.

The proteins are preferably selected from the group comprising insulin, calcitonin, ACTH, glucagon, somatostatin, somatotropin, somatomedin, parathyroid hormone, erythropoietin, hypothalamic release factors, prolactin, thyroid-stimulating hormone, endorphins, enkephalins, vasopressins, non-naturally occurring opiates, superoxide dismutase, antibodies, interferons, asparaginase, arginase, arginine deaminase, adenosine deaminase, ribonuclease, trypsin, chymotrypsin and pepsin.

Another aspect of the invention is a process for the in vitro production of biodegradable polymer particles, wherein the process comprises providing a solution suited to polymer particles formation with at least one substrate, introducing into the solution a protein which is suited to controlling the size of the polymer particles and introducing at least one further protein which is involved in the formation of the polymer particles. The in vitro process also offers the advantage that the size of the polymer particles may be controlled as early as during production of the polymer particles and subsequent costly and time-consuming size determination and separation of the polymer particles formed into individual size classes is avoided.

The at least one further protein used here, which is involved in the formation of the polymer particles, is a polymer synthase, wherein this polymer synthase is preferably selected from the group comprising the polymer synthase from *R. eutropha, P. oleovorans, P. putida* and *P. aeruginosa*.

In contrast with in vivo synthesis, an in vitro synthesis, in which proteins and enzymes isolated from microorganisms are used in the laboratory, is normally very costly as both the enzymes and, in some cases, also the enzyme substrates must be isolated and purified beforehand. In one particular embodiment of the present invention for the in vitro synthesis of the biocompatible, biodegradable polymer particles, there is added to the solution suited to polymer particle formation at least one fatty acid, particularly preferably a β-mercapto fatty acid and/or a β-amino fatty acid and an acyl CoA oxidase or other oxidising and activating enzymes for the formation of the polymer particles. Using these substrates instead of R/S-3-hydroxy fatty acids and acyl CoA synthetase results in a CoA recycling system, in which the acyl CoA oxidase will activate and oxidise the fatty acid while consuming CoA and hydrolysing ATP. During polymerisation, the polymer synthase eliminates CoA, which may then in turn be used by the acyl CoA oxidase. An appreciable reduction in the costs of this in vitro process may be achieved as a consequence.

Another advantage of the in vitro process for the production of polymer particles is that the at least one substrate is added to the solution suited to polymer particle formation in such a quantity that it is sufficient to ensure control of the size of the polymer particles.

Moreover, the size of the polymer particles formed may also additionally be controlled by adding the polymer synthase to the solution in a quantity which is sufficient to ensure control of the size of the polymer particles formed. As in the in vivo process, the in vitro process also comprises further possibilities for controlling polymer particle size still more accurately, so increasing the yield of polymer particles of the desired size and making the process more efficient and cost-effective.

In the in vitro process, however, particle size is actually controlled by introducing a protein which controls the size of the polymer particles into the solution, which protein is derived from the family of phasin-like proteins and is preferably selected from the group comprising the phasin from *Ralstonia eutropha* and the phasin from *Pseudomonas oleovorans*.

By selecting the at least one substrate as well the enzymes used, it is also possible, as in the in vivo process, to regulate the composition of the polymer and so obtain polymer cores with different properties. When more than one substrate is used, it is for example possible, depending on the type of polymer formed from the enzymes, to obtain polymer particles with a different composition of the polymer core. As already described further above, the polymers produced in this manner impart the most varied properties to the polymer particles.

In the in vitro process for the production of the polymer particles, the composition of the lipid layer on the surface of the polymer particle is controlled by adding at least one amphiphilic molecule from the group of phospholipids and ether lipids to the solution (In the absence of additional amphiphilic molecules, the particles obtained in vitro are surrounded only by proteins, which constitutes another type of particles.). In this manner, it is possible, for example, to produce polymer particles with a specific surface charge which is specifically adjusted to the biological membrane which is subsequently to be crossed in the animal body. The advantage of modifying the lipid layer of the shell membrane in the in vitro process is that it is possible to dispense with subsequent modification of the lipid layer, as in the in vivo process. Since the amphiphilic molecules, such as for example phospholipids or ether lipids, are already added to the starting solution, a lipid layer of the desired composition is obtained from the outset.

Another aspect of the in vitro process, which is also used in the in vivo process, is that at least one pharmaceutically active substance is added to the solution suited to polymer particle formation. Said substance is incorporated into the polymer particle during polymer particle synthesis and may subsequently be released into the animal body by diffusion through the particle matrix or by degradation of the polymer particle. The latter-stated variant has the further advantage in the polymer particles produced by the process according to the invention that the rate of biodegradation of the polymer particles may be regulated by the above-described control of the composition of the polymer core. In this manner, continuous release of the active ingredient over a specific period is possible.

Apart from the incorporation of active ingredients into the growing polymer particles, functionalisation proceeds, as in the in vivo process, by selecting at least one of the proteins introduced into the solution suited to polymer particle formation in such a manner that the at least one introduced protein comprises a polymer particle binding domain and at least one binding domain, wherein the at least one binding domain is capable of binding a biologically active substance and/or a coupling reagent. The proteins used in this case for the formation of the polymer particles in the in vitro process may be obtained from the in vivo process described further above and they then exhibit, depending on the type of production described above, the corresponding properties. They are then added to the solution suited to polymer particle formation, where they are involved in the formation of the polymer particles. As in the in vivo process, the polymer particles produced in this manner may also additionally be modified after the production thereof by subsequent modification with the coupling reagents already described further above or by addition of biologically active substances which bind to the binding domain of the proteins which have been bound to the surface of the polymer particles.

The invention furthermore comprises a polymer particle of defined size, with a surface layer of amphiphilic molecules, into which [is introduced] at least one protein which is selected from the group comprising a polymer depolymerase, a polymer regulator, a polymer synthase and a particle size-influencing protein, wherein the at least one protein comprises a polymer particle binding domain and a binding domain which is capable of binding a biologically active substance and/or a coupling reagent and which protein, in a preferred embodiment, is produced according to the above-described process.

Thanks to their advantageous properties, the polymer particles of the present invention are particularly suitable for the production of a pharmaceutical preparation, a pesticide or a herbicide, wherein the pharmaceutical preparation is preferably suitable for the treatment of diseases of the central nervous system. The possibilities for modification of the polymer particles described by the present process allow the conditions to be met for passage through the BBB.

The control of particle size, control of the composition of the shell membrane and in particular also the functionalisation of particle surface mean that these biodegradable polymer particles are a suitable transport vehicle for biologically active substances of all kinds and moreover enable targeted transport of the polymer particles to their site of action. Multifunctionalisation makes it possible, for example, simultaneously to bind not only at least one pharmaceutical active substance to the particle surface but also an antibody, the binding specificity of which enables precise guidance to the target site. These and further advantages are explained in greater detail in the following exemplary embodiments.

The abbreviations relate to the following proteins:
A: polymer depolymerase
B: phasin (name of the coding gene in *R. eutropha*: phaP, in *P. oleovorans*: phaF)
C: polymer synthase
D: phospholipid
E: polymer regulators (for example phasin repressor (PhaR from *R. eutropha*)

Figure 2:
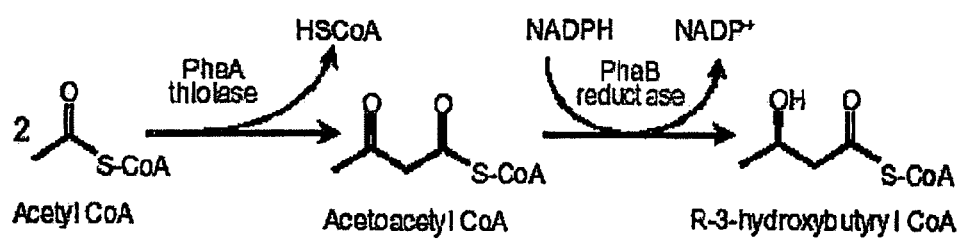
Figure 2:
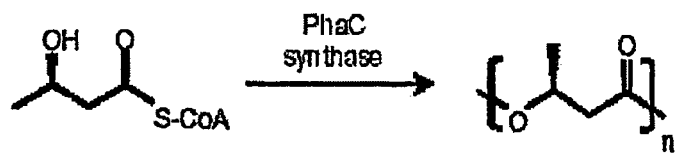

FIG. 2 shows an example of synthesis of one of the possible biodegradable polymers in *R. eutropha*. The simple polyhydroxy alkanoate polyhydroxybutyric acid (PHB) is produced in a three-stage process starting from the substrate acetyl CoA. The C4 repeat unit in PHB is β-hydroxybutyric acid. The final step in the synthesis results in the formation of the polymer particle with the polymer synthase bound to the surface thereof.

Figure 3:
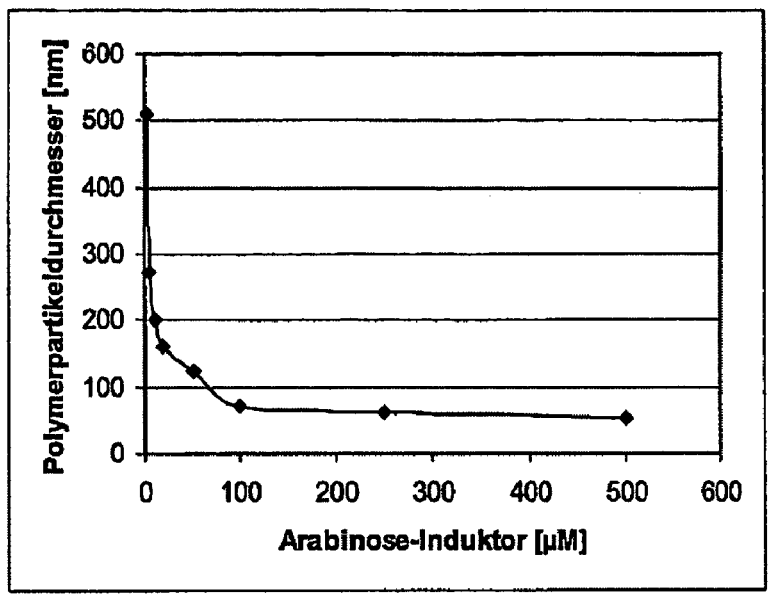
Figure 4:
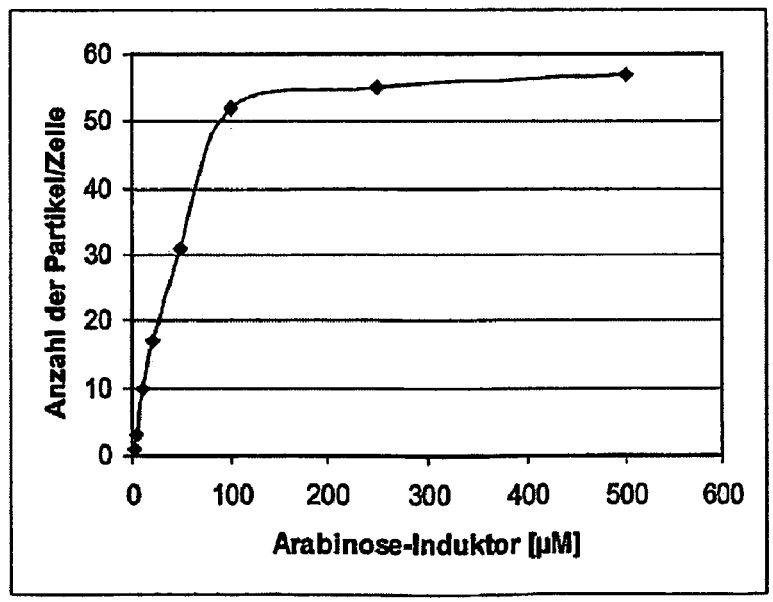

FIGS. 3 and 4 show the results from the in vivo experiments.

FIG. 3 here describes the behaviour of polymer particle diameter with enhanced phasin expression (increased quantity of inducer in the solution), while FIG. 4 describes the behaviour of the polymer particle count in the cell with enhanced phasin expression (increased quantity of inducer in the solution).

Figure 5:
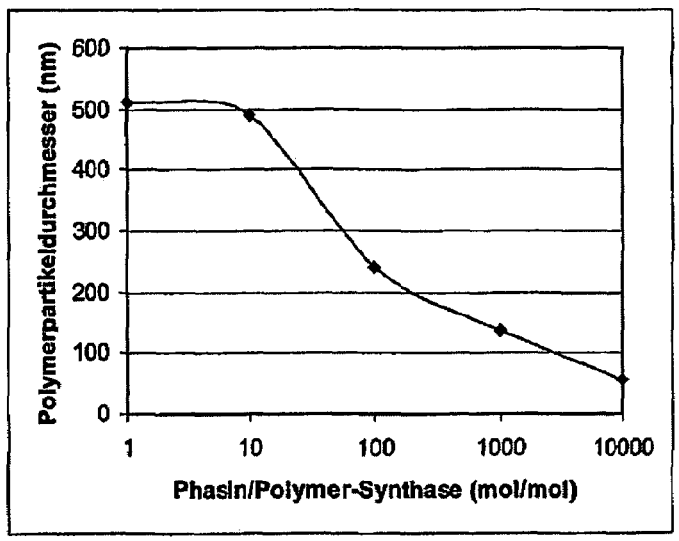
Figure 6:
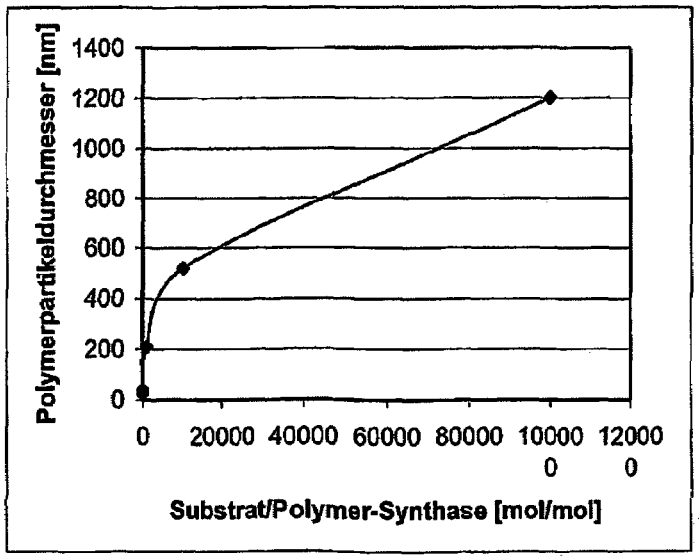

FIGS. 5 and 6 show the results of the in vitro experiments.

FIG. 5 describes the influence of the quantity ratio of phasin to polymer synthase on polymer particle diameter, while FIG. 6 describes the influence of the ratio of substrate to polymer synthase on polymer particle diameter.

Figure 7:
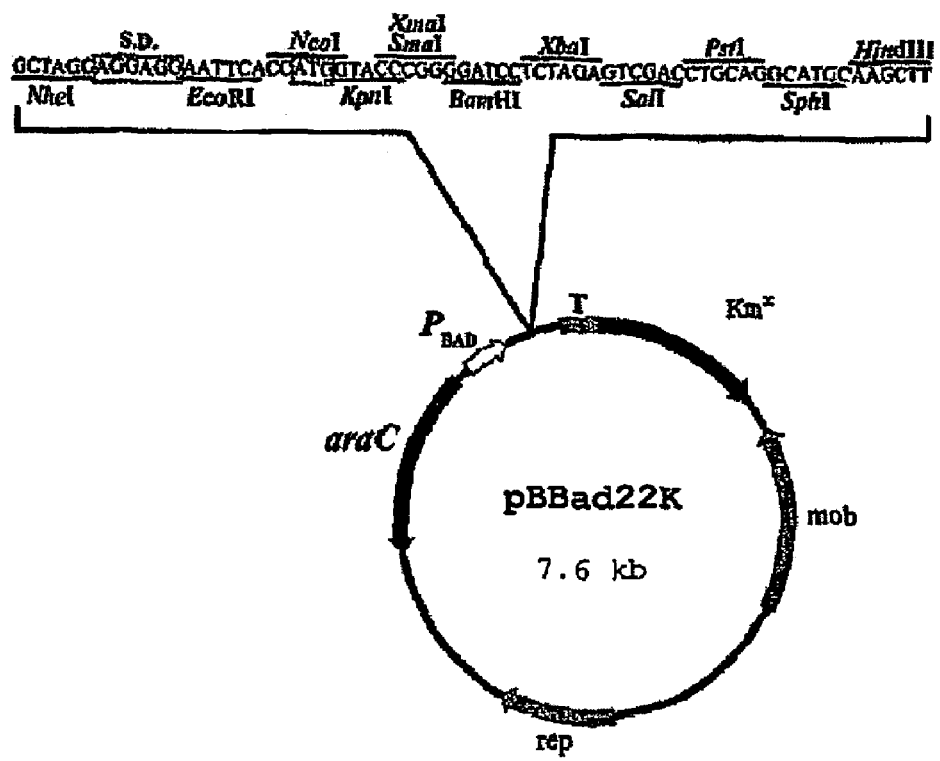

FIG. 7 shows the vector pBBad22K (Sukchawalit, R. et al, FEMS Microbiol Lett. 1999, Vol. 181(2), pp. 217-223) which is used as the starting plasmid in the construction of plasmids pBBad-P (which bears the gene phaP from *R. eutropha*) and pBBad-F (which bears the gene phaF from *P. oleovorans*).

Figure 8:
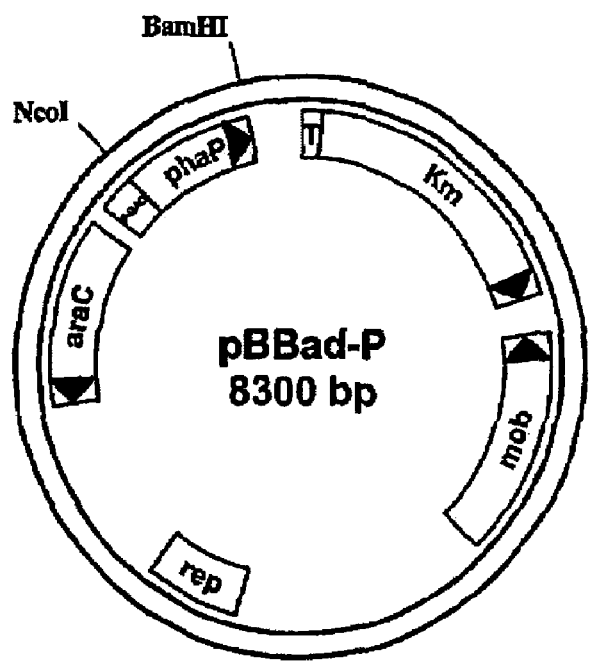

FIG. 8 shows the vector pBBad-P which bears the gene phaP for the expression of the particle size-determining protein phasin from *R. eutropha*.

Figure 9:
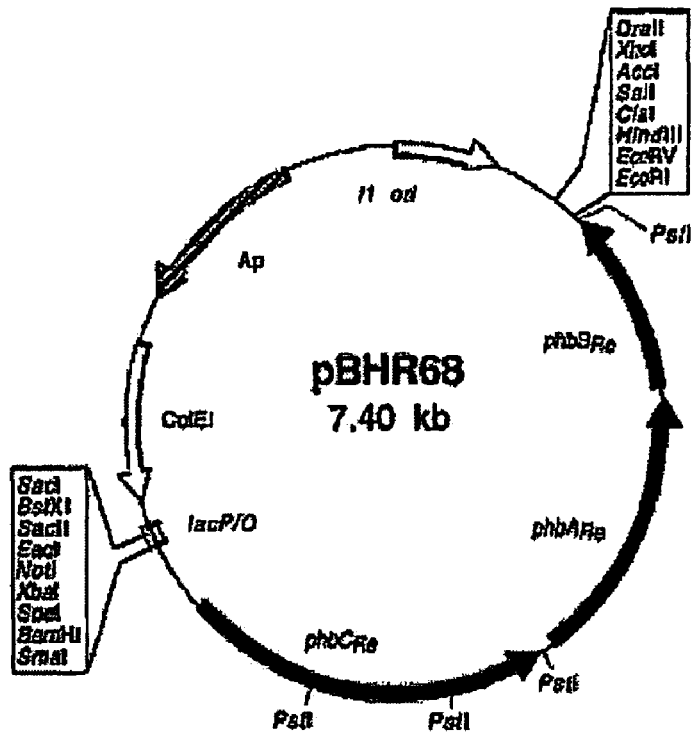

FIG. 9 shows the plasmid pBHR68 (Spiekermann, P. et al., Arch. Microbiol. 1999, Vol. 171, pp. 73-80) which imparts storage of the polymer (polyhydroxybutyric acid), said plasmid bearing the genes $phB_{Re}$, $phbA_{Re}$ and $phbC_{Re}$ from *Ralstonia eutropha* which form the biosynthesis operon for the expression of phaA thiolase, phaB ketoacyl reductase and phaC synthase.

Figure 10:
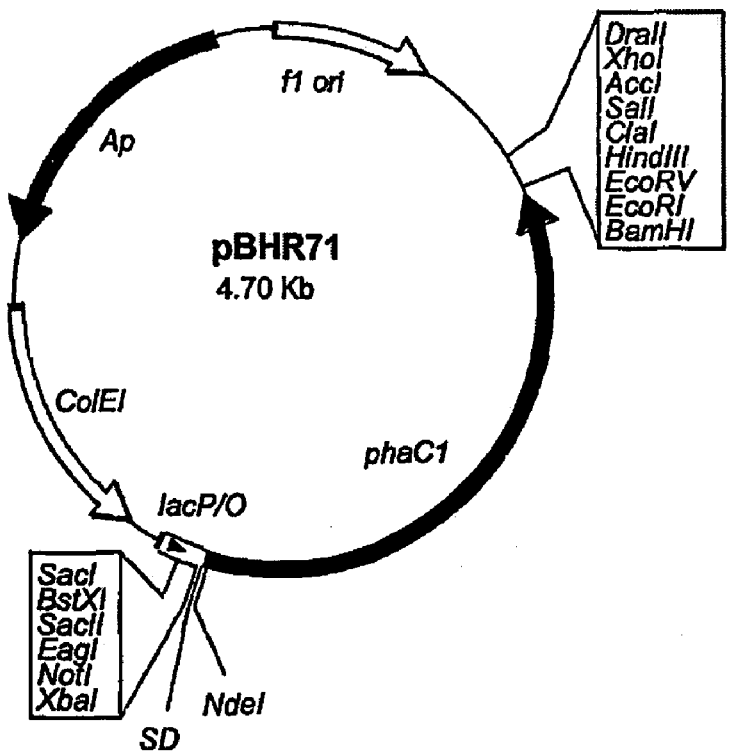

FIG. 10 shows the plasmid pBHR71 (Langenbach, S. et al., FEMS Microbiol. Lett. 1997, Vol. 150, pp. 303-309) which imparts storage of the polymer (polyhydroxy alkanoates), said plasmid bearing the gene phaC1 for expression of polymer synthase.

Figure 11:
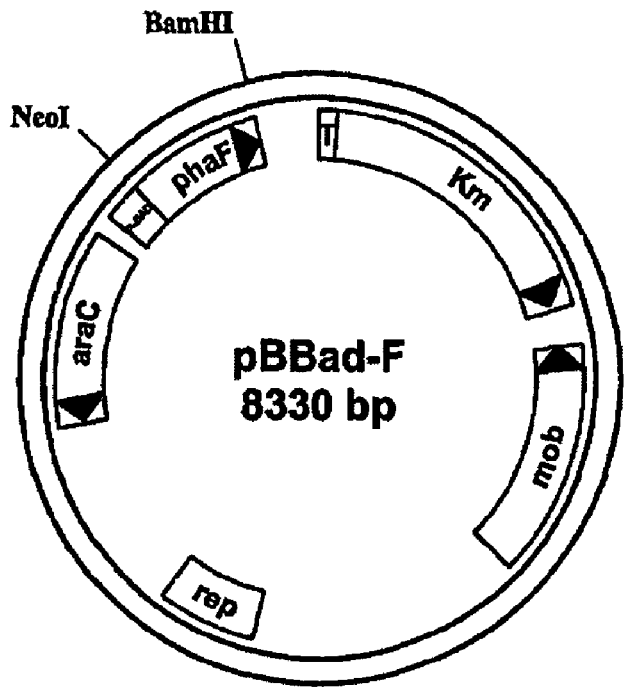

FIG. 11 shows the vector pBBad-F which bears the gene phaF for expression of the particle size-determining phasin-like protein from *P. oleovorans*.

Figure 12:
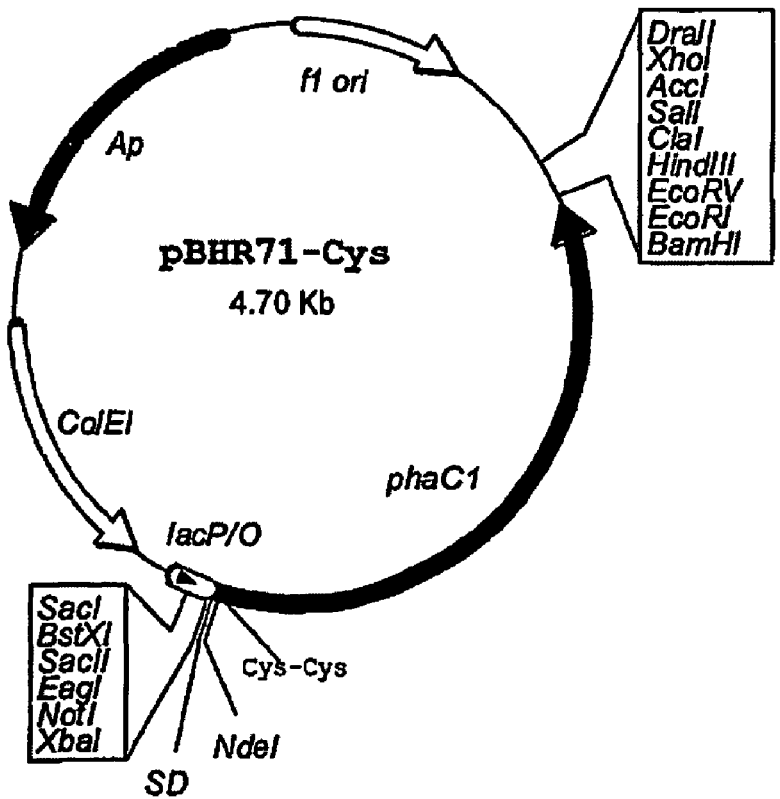

FIG. 12 shows the vector pBHR71-Cys which has been constructed starting from plasmid pBHR71 from FIG. 10. In this structure, the gene phaC1, which codes for polymer synthase, bears two cysteine residues on the N-terminus in order to enable direct binding of biologically active substances or the binding of biologically active substances via coupling reagents.

Figure 13:
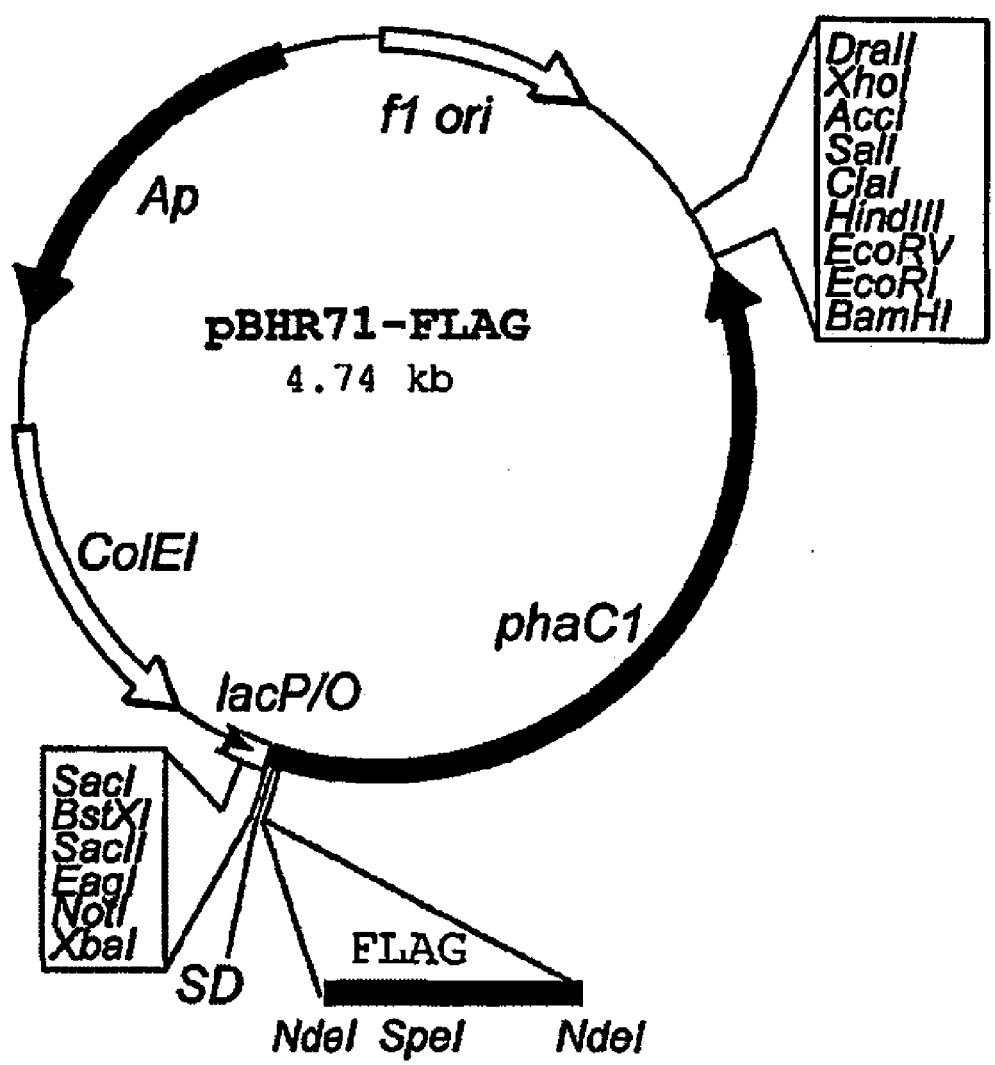

FIG. 13 shows the vector pBHR71-FLAG, which has likewise been constructed starting from plasmid pBHR71 from FIG. 10. In this structure, the gene phaC1, which codes for polymer synthase, bears two FLAG epitopes on the N-terminus. This enables not only in vivo incorporation of gene sequences for functional proteins via the SpeI restriction site of the FLAG gene sequence but also the attachment of coupling reagents and/or biologically active substances in vitro onto the already expressed polymer synthase. The biologically active substances used, which are bound directly or via coupling reagents, impart binding to the target site (for example cell surface) or biological activity, in particular enzymatic activity.

EXAMPLE 1

Control of the Size of the In Vivo Produced Biodegradable Polymer Particles

EXAMPLE 1.1

Production of Polymer Particles in *R. eutropha*

The biodegradable polymer particles are produced using a "knock-out" mutant of *Ralstonia eutropha* (formerly *Alcaligenes eutrophus*) York et al. (York, G. M. et al. J. Bacteriol. 2001, Vol. 183, pp. 4217-4226) which exhibits a defect with regard to the gene which codes for expression of the surface protein phasin on the polymer particles (phaP(−)), as a consequence of which the organism is no longer capable of expressing the phasin which is coded by the phaP gene. The biodegradable polymer particles may moreover also be produced using microorganisms which do not contain this gene and the further genes required for the biosynthesis of polymer particles. Possible examples of such microorganisms would be *Escherichia coli*, and *Halobiforma haloterrestris*. One exemplary embodiment uses *Escherichia coli* (see Example 2), which is naturally not capable of producing the biodegradable polymer particles already described above.

The latter-stated microorganisms are then transformed with a vector which, in the case of *R. eutropha*, contains the phaP gene which codes for phasin and contains the promoter sequence. This gene is controlled by an inducible promoter, preferably a BAD promoter which is induced by arabinose.

Cloning Steps

Cloning is performed using the DNA sequence from *R. eutropha* which codes for phaP, this sequence being listed in the "GenBank" under number AF079155 (Hanley, S. Z. et al., FEBS Letters 1999, Vol. 447, pp. 99-105). This sequence is inserted in the NcoI/BamHI restriction site of the vector pBBad22K (Sukchawalit, R. et al., FEMS Microbiol Lett. 1999, Vol. 181(2), pp. 217-223, c.f. FIG. 7) which contains an inducible promoter ($P_{BAD}$). For the purposes of cloning, the corresponding NcoI and BamHI restriction sites are inserted into the sequence which codes for phasin by PCR mutagenesis by means of the primers 5'-aaaggccccatggtctcaccccg-gaaca-3' (SEQ ID No. 1, NcoI restriction site in bold) and 5'-aaaggccggatcctcagggcactaccttcatcg-3' (SEQ ID No.2, BamHI restriction site in bold). The resultant DNA fragment of SEQ ID No. 3 is hydrolysed with the restriction enzymes NcoI and BamHI and ligated into the likewise hydrolysed vector pBBad22K (FIG. 7). The plasmid, which now contains the nucleotide sequences for the protein phasin, is hereinafter designated pBBad-P (FIG. 8). This plasmid is transferred into the microorganism by means of the transformation techniques described in the prior art for the corresponding organism. The inducer of the BAD promoter of pBBad-P is arabinose, which makes it possible to achieve quantitative control of the expression of this gene in the microorganisms used. This control mechanism is used to control the expression of the phasin gene and, by means of the quantity of phasin present in the cell, ultimately to control the size of the polymer particles.

EXAMPLE 1.2

Production of Microorganisms for the Production of Polymer Particles which were not Originally Capable of Forming Polymer Particles In microorganisms which were not originally capable of producing polymer particles of this type, an additional or the same vector contains further genes which are involved in the formation of the polymer particles. The number and type of the necessary genes which must be introduced into a microbial organism for production of the polymer particles are determined by the basic make-up of the organism used. In the simplest case, for example in E. coli, at least one thiolase, a reductase and a polymer synthase are necessary in order to produce polymer particles in the manner shown in FIG. 2. If organisms are used which comprise specific mutations, such as for example the E. coli strain from Example 4, fewer than the above-stated genes are sufficient to enable production of the polymer particles. The same applies if the organism is already supplied with certain precursor substrates from the metabolic pathway for polymer synthesis.

If a further plasmid is used to introduce into the cell the genes necessary for formation of the polymer particles, the plasmid pBHR68 (FIG. 9), which contains the 5.2 kb SmaI/EcoRI fragment from the chromosomal DNA of R. eutropha, is particularly suitable. This plasmid contains the biosynthesis operon for the production of biodegradable polymer particles from R. eutropha (Spiekermann, P. et al., Arch. Microbiol. 1999, Vol. 171, pp. 73-80).

EXAMPLE 1.3

Control of Particle Size by Means of the pBBad-P Vector

The microorganisms modified in this manner are incubated at 30° C. in Luria Broth medium. Induction of the promoter with arabinose proceeds in the late logarithmic growth phase. 24 h after incubation, the size of the particles in the cells is determined. To this end, the cells are separated from the nutrient medium by centrifugation and disrupted. Microscopic determination of polymer particle size is then performed by tunneling electron microscopy in combination with analytical gel filtration chromatography. The polymer particle count is determined by investigating the intact cells under a light microscope and counting the number of the polymer particles per cell.

As is demonstrated by the results, by controlling expression it is possible to control both the average size of the polymer particles formed (c.f. FIG. 3) and the average number thereof (c.f. FIG. 4) in the individual cells. Increasing the copy number of phasin in a controlled manner brings about a decrease in the average polymer particle diameter with a simultaneous increase in the average number of polymer particles. In this manner, it is possible to bring about a distinct increase in the yield of polymer particles with the desired diameter. This makes production of the polymer particles quicker and more cost-effective.

EXAMPLE 1.3

Control of Particle Size by Substrate Availability

Another mechanism for controlling the size of the polymer particles is to regulate the availability of substrates or of the polymer synthase which are required for synthesis of the polymer particles. Availability of the polymer synthase may be controlled by means of antisense methods, by genetic regulation or by the availability of the substrates which are required for formation of the polymer synthase in the nutrient medium.

One example of particle size regulation by the availability of a substrate in the nutrient medium is an experiment in which the concentration of the carbon source present is reduced in order consequently to control the diameter of the polymer particles formed. To this end, an E. coli strain which contains the above-stated plasmid pBHR68 (FIG. 9) with the biosynthesis operon for the production of biodegradable polymer particles from R. eutropha (FIG. 8), is grown in M9 medium with 1.5% (w/v) glucose at 30° C. At the beginning of the stationary growth phase, the concentration of the carbon source is reduced to 1/50th of its original value by adding M9 medium without glucose and the microorganisms are incubated under otherwise constant growth conditions for a further 20 h. On completion of the test, the microorganisms contain polymer particles with a diameter of on average 130 nm.

EXAMPLE 2

Influencing the Composition of the In Vivo Produced Polymer Particles

The composition of the biodegradable polymer particle may be modified by introducing into the cell, in addition to the gene coding for phaP, further genes which code for enzymes which provide substrates for the synthase, in particular thiolases or further polymer synthases. As a result, during formation of the polymer particles, the cell is capable of incorporating a series of different monomers into the growing polymer chain and so produce polymer particles having a core which consists of differently composed polymers.

Examples which may be mentioned in this connection are various polymer synthases which, due to their substrate specificity, incorporate 3-hydroxy fatty acids (C4-C16) differently into the growing polymer chain in both the in vivo and the in vitro process. It is, for example, possible to use the polymer synthase from R. eutropha, which produces biodegradable polymer chains from C4 fatty acids (C4), polymer synthases from Aeromonas punctata (C4 and C6), Thiocapsa pfennigii (C4 and C8) and P. aeruginosa (C6 to C14). Simultaneously introducing two or more polymer synthases into the cell also makes it possible to produce polymer particles with the most varied properties. In a continuous batch, new polymer synthases with modified substrate specificity may also be obtained by random mutagenesis (in vitro evolution).

The composition of the polymer particles formed may also be influenced in other manners. Providing different carbon sources, precursors of different carbon sources and intermediates of the metabolic pathway leading to formation of the polymer particles likewise have an impact on the nature of the polymer formed. Moreover, the metabolic pathways involved in the formation of the polymer particles may be controlled by inhibitors, the use of knockout mutants of the metabolic pathway in question and the expression of enzymes which result in the metabolic pathway in the formation of other intermediate or final products.

The following enzymes are used to influence fatty acid metabolism, these enzymes having the property of modifying the intermediates of fatty acid metabolism and providing different products, for example. fatty acids with different side chains, for the formation of the polymer particles: (R)-specific enoyl-CoA hydratases, transacylases and ketoacyl-CoA/ ACP reductases. These enzymes have a different specificity with regard to the chain length of the (R)-hydroxyacyl-CoA substrate provided for the polymer synthase. As a consequence, building blocks with differing side chain lengths are obtained in the polymer, resulting in polymers of different compositions.

However, introducing additional enzymes into the cell is not the only way of influencing the metabolic pathway—inhibitors of the metabolic pathway may also be added to the medium. Examples of such inhibitors are acrylic acid and triclosan (synonyms: TCC or 5-chloro-2-(2,4-dichlorophenoxy)phenol), to name but a few.

EXAMPLE 3

In Vivo Production of Biodegradable Polymer Particles from (R)-3-Hydroxybutyric Acid with a Highly Crystalline Core This experiment was performed using an *E. coli* strain which contains the plasmid pBBad-P and the plasmid pBHR68 already stated in Example 1. Culturing was performed under the conditions stated in Example 1 with glucose as the carbon source. The polymer particles formed consist of (R)-3-hydroxybutyric acid and have a diameter of 50 to 500 nm, depending on how much inducer (arabinose) is added to the medium. The average size of the polymer particles formed in this manner here varies by only approx. 20 to 50 nm. In order to clarify the control characteristics achieved by the phasin introduced by means of the pBBad-P plasmid, the experiment is repeated with the above-stated *E. coli* strain without the pBBad-P plasmid. In this case, polymer particles with a diameter of 150-250 nm are obtained. In comparison with the control experiment, controlling particle size by means of the phasin enables the production of much larger but above all also much smaller polymer particles.

Further fractionation of the polymer particles by size may then proceed by processes known in the prior art, such as for example, exclusion chromatography, density gradient centrifugation, or ultrafiltration in 5 mM phosphate buffer (pH 7.5).

EXAMPLE 4

In Vivo Production of Biodegradable Polymer Particles from (R)-3-Hydroxy Fatty Acids with a Core of Low Crystallinity In this experiment, biodegradable, elastomeric polymer particles having a core of (R)-3-hydroxy fatty acids are produced in *E. coli*. The polymer chains are on average made up of 6 to 14 carbon atoms. This is achieved by regulated expression of the phaF gene from *P. oleovorans* in *E. coli*, which is very similar to the phasin-coding gene phaP from *R. eutropha* and to the gene for polymer synthase from *P. aeruginosa* (phaC). In this Example, the expression product of the gene phaF is used to control particle size. The polymer particles may be produced in *E. coli* cells with modified fatty acid metabolism solely by the polymer synthase (phaC) of the pseudomonads (Langenbach, S. et al., FEMS Microbiol. Lett. 1997, Vol. 150, pp. 303-309). Fatty acid metabolism is modified in such a manner that, when fatty acids are used as the carbon source, CoA-activated intermediates (for example enoyl-CoA) of fatty acid β oxidation are accumulated which in turn act as precursors for polymer synthesis. To this end, fadB mutants of *E. coli* are used (Langenbach, S. et al., FEMS Microbiol. Lett. 1997, Vol. 150, pp. 303-309) or inhibitors are used which correspondingly inhibit fatty acid metabolism (for example acrylic acid; Qi, Q. et al., FEMS Microbiol. Lett. 1998, Vol. 167, pp. 89-94). The otherwise required ketoacyl reductase and the thiolase are no longer necessary when using the mutants or inhibited microorganisms. Enoyl-CoA hydratases intrinsic to *E. coli* then catalyse the formation of R-3-hydroxyacyl-CoA from enoyl-CoA. This is then converted by the polymer synthase into poly-(R)-3-hydroxy fatty acid, which forms the polymer core of the polymer particle formed.

Cloning

The phaF gene of *P. oleovorans*, which has already been described by Prieto et al. (Prieto, M. A. et al., J. Bacteriol. 1999, Vol. 181(3), pp. 858-868) and is listed in the "GenBank" database under number AJ010393, is transformed into *E. coli* using vector pBBad-F (FIG. 11). This vector is obtained on the basis of vector pBBad22K (FIG. 7). The individual cloning steps here correspond to those described in Example 1. The phaF gene is cloned into the NcoI/BamHI restriction site of the vector pBBad22K. The primers used for PCR mutagenesis of the above-stated phaF gene have the following sequences: 5'-aaagggccatggctggcaagaagaattc-cgagaa-3' (SEQ ID No. 4, NcoI restriction site in bold) and 5'-aaaggggatcctcagatcagggtaccggtgcctgtctg-3' (SEQ ID No. 5, BamHI restriction site in bold). The resultant DNA fragment of SEQ ID No. 6 is then cloned into the above-described plasmid pBBad22K. The plasmid which now contains the sequence for phaF is hereinafter designated pBBad-F (FIG. 11). In addition to this plasmid, the plasmid pBHR71 containing the nucleotide sequence for polymer synthase (FIG. 10; Langenbach, S. et al., FEMS Microbiol. Lett. 1997, Vol. 150, pp. 303-309) is also transformed into *E. coli*.

The carbon source used for the subsequent expression is the fatty acid decanoic acid. Expression of the phasin phaF gene is again controlled by means of the inducer arabinose. The test is here performed as already described in Example 1. Depending on the quantity of inducer previously used, the polymer particles formed in this way have a diameter of 100-500 nm.

EXAMPLE 4

Control of the Size of the In Vitro Produced Biodegradable Polymer Particles

The size of the biodegradable polymer particles formed is also controlled in in vitro production by the availability of the polymer synthase, of phasin or phasin-like proteins and the availability of the substrates and metabolic intermediates.

The necessary enzymes and substrates must first be made available for the in vitro batch for the production of biodegradable polymer particles. The recombinant polymer synthase from *R. eutropha* or *P. aeruginosa* is used for this test (Gerngross, T. U. and Martin, D. P., Proc. Natl. Acad. Sci. USA 1995, Vol. 92, pp. 6279-6283; Qi, Q. et al., Appl. Microbiol. Biotechnol. 2000, Vol. 54, pp. 37-43), which are purified by affinity chromatography (with His-Tag fusion or $Ni^{2+}$-NTA agarose). The polymer particle size-determining proteins from *R. eutropha* and *P. aeruginosa*, for controlling particle size, are purified in a similar manner. In order to express this protein in *R. eutropha*, the same vector is used which has already been used in Example 1 to express the phasin gene. The reaction batch for in vitro production of the biodegradable polymer particles additionally contains, apart from the polymer synthase and the polymer particle size-determining protein phasin: R-3-hydroxybutyryl-CoA or R-3-hydroxydecanoyl-CoA as substrate for synthesis of the polymer particles, 50 mM phosphate buffer (pH 7.5), 1 mM $MgCl_2$ and 5% glycerol (v/v) for stabilisation. Due to the use of R-3-hydroxybutyryl-CoA or R-3-hydroxydecanoyl-CoA as precursors for the polymer synthase, it is not necessary to use the thiolase and the reductase (c.f. FIG. 2).

The results of FIG. 5 show the influence of the quantity ratio of phasin to polymer synthase on polymer particle diameter, while FIG. 6 shows the influence of the ratio of substrate to polymer synthase on polymer particle diameter. These results also show that polymer particle size regulation may be regulated by the quantity of polymer synthase present. Effective regulation of particle size may accordingly be achieved by means of the process according to the invention.

EXAMPLE 5

Influencing the Composition of the In Vitro Produced Polymer Particles

EXAMPLE 5.1

Influencing Polymer Composition

The composition of the biodegradable polymer particle may be modified by adding different substrates to the reaction batch and/or by using in each case different polymer synthases with a different substrate spectrum (c.f. Example 2). In this manner, a series of different monomers is incorporated into the growing polymer chain during formation of the polymer particles and polymer particles with a different polymer composition are produced. Due to the use of the polymer synthase from *P. aeruginosa*, R-3-hydroxy fatty acid building blocks with 6-14 C atoms are incorporated into the growing polymer chain. If, for example, only one substrate is supplied, homopolymeric polymer particles are obtained when using the polymer synthase from *P. aeruginosa*.

Further examples of how the composition of the polymer particles may be modified are stated in Example 2.

EXAMPLE 5.2

Influencing the Membrane Composition of the Polymer Particles

For the purposes of subsequent fusion with the membrane of a cell, into which an active ingredient is to be introduced, for example, it must be possible to control the composition of the phospholipid layer on the surface of biodegradable polymer particles. This regulation is achieved in in vitro production (Example 4) of the biodegradable polymer particles right from the provision of the solution suited to polymer particle formation. The membrane can be individually tailored to the corresponding requirements by adding a mixture of different amphiphilic molecules.

Phospholipids are added to the in vitro reaction batch. A defined number of molecules of the polymer synthase are now involved in the formation of the polymer particles. As polymerisation proceeds, the polymer particles according to the invention become larger and the polymer synthases on the surface are no longer able completely to shield the surface of the polymer particles. As a result, hydrophobic zones (of polymer) are exposed, to which amphiphilic molecules spontaneously attach themselves.

In the case of in vivo produced particles, the phospholipid layer which is already present must first be removed. To this end, acetone extraction is performed or phospholipases or non-denaturing detergents are used to destroy the phospholipid layer. Then, as already described above, a mixture of the appropriate amphiphilic molecules is added to the now virtually lipid-free polymer particles. Negatively charged phospholipids or phosphatidyl choline are preferably used here. In one exemplary embodiment of purposeful control of membrane composition, the polymer particles are suspended in PBS containing 1% octyl glycoside (pH 7.5) and dialysed against an excess of phosphatidyl choline while being stirred. The resultant particle surface is particularly well suited to fusion with brain capillary endothelial cells (BCEC).

EXAMPLE 5.3

Incorporation of Various Substances into the Growing Polymer Particles

Uptake of substances into the core of the biodegradable polymer particle has already been qualitatively investigated with the assistance of the lipophilic fluorescent dye Nile Red (Sigma, St. Louis, Mo. USA) or Rhodamine 123 (Spiekermann, P. et al., Arch. Microbiol. 1999, Vol. 171, pp. 73-80). If, during in vivo or in vitro production, as described above, the fluorescent dye Nile Red is added to the medium or the reaction batch, dyeing of the polymer particles produced can be observed, i.e. dyeing of the polymer particles begins as early as during the synthesis thereof and even before isolation from the cell.

If active ingredients with a pharmaceutical action are added, they may be incorporated into the polymer core of the particle. For example, the nonpolar antitumour agent paclitaxel is added to the reaction batch in an in vitro experiment for the production of the polymer particles. The water-insoluble paclitaxel is dissolved and concentrated in the hydrophobic polymer core of the polymer particles. Paclitaxel is here merely added to the solution for the formation of the polymer particles, whereupon the active ingredient is concentrated in the particles. This is verified once the polymer particles have formed by removing them from the reaction batch and investigating the solution for the presence of paclitaxel by means of HPLC. The decrease in paclitaxel concentration in the solution here shows that it has been incorporated into the polymer particles. As the polymer particles biodegrade in the organism, the active ingredient is subsequently released. A reaction batch without polymer particles is used as a control, wherein in this case there is no decrease in the paclitaxel concentration in the solution suited to polymer particle formation.

EXAMPLE 6

Functionalisation of the Particle Surface

Biologically active substances can be bound to proteins which are already located on the surface of the polymer particles. All the proteins stated in FIG. 1 may be considered. This results in a plurality of "cross-linking"-strategies, which enable covalent linkage of the biologically active substance via proteins which are bound to the particle surface.

EXAMPLE 6.1

Purposeful Modification of a Surface Protein for Attachment of a Pharmaceutical Active Ingredient One example of functionalisation of the polymer particles is the attachment of hydrazone-bound doxorubicin (hydrazone-bound doxorubicin has been described by King, H. D. et al., Biconjugate Chem. 1999, Vol. 10, pp. 279-288) to the polymer synthase PhaC1 from *P. aeruginosa*, which is bound on the surface of the polymer particles and contains two N-terminally inserted cysteine residues. These cysteine residues form the binding domain of the polymer synthase, by means of which the biologically active substances may be bound.

Cloning

The triplets coding for the cysteine residues are cloned by PCR mutagenesis into the gene coding for PhaC1, which is then cloned into the XbaI and BamHI restriction site of the plasmid pBHR71 shown in FIG. 10. The restriction sites for XbaI and BamHI are also inserted into the gene in this PCR mutagenesis. The primers used for the PCR mutagenesis of the PhaC1-coding gene have the following sequences: primer for the N-terminus 5'-gggctctagaaataaggagatatacatat gtgttgtaagaacaataacgagctt-3' (SEQ ID No. 7, XbaI restriction site in bold, Cys triplet underlined) and primer for the C-terminus 5'-aaacgcggatccttttcatcgttcatgca-3' (SEQ ID No. 8, BamHI restriction site in bold). The DNA fragment so obtained of SEQ ID No. 9 is then hydrolysed with XbaI and BamHI and ligated into the similarly hydrolysed plasmid pBHR71. The resultant plasmid, designated pBHR71-Cys (FIG. 12), is transformed into *E. coli* by means of known techniques, where it then enables the formation of polymer particles bearing a polymer synthase on the surface thereof, which polymer synthase bears two cysteine residues for the attachment of various substances, in particular pharmaceutical substances.

EXAMPLE 6.1.1

Attachment of Doxorubicin (Syn.: Hydroxyl Daunorubicin)

Hydrazone-mediated "cross-linking" may now proceed via these surface-exposed cysteine residues. To this end, the following method is used: 100 mg of the isolated polymer particles (total volume 1 ml) to which the polymer synthase is bound are incubated for 3 h at 37° C. in helium-perfused PBS (pH 7.5) and 5 mM dithiothreitol (DTT). This treatment reduces the disulfide bridges in the polymer synthase. The low molecular weight compounds are then removed by 30 minutes' centrifugation at 4° C. and 40,000×g. The reduced polymer particles are then suspended with 1 ml of PBS buffer (pH 7.5), which contains 10 µmol of the hydrazone-bound doxorubicin, and incubated for 30 min at 4° C. After this period, centrifugation is again performed under the above-stated conditions in order to wash the treated polymer particles. Unbound doxorubicin is detected by subsequent HPLC and the successful attachment to the polymer synthase is verified by the reduced concentration.

EXAMPLE 6.2

Attachment of Biologically Active Substances, in Particular Pharmaceutical Active Ingredients to the Binding Domain of the Polymer Particles Active ingredients may also be bound to the polymer particles by being bound via the binding domain onto the proteins bound to the surface of the polymer particles. To this end, a binding domain must first of all be created. Binding of biologically active substances is achieved by genetic modification of surface-bound proteins of the polymer particles (such as for example polymer depolymerase, phasin or phasin-like proteins, polymer synthase, polymer regulator), such that these proteins form an outwardly directed binding domain by means of which a coupling reagent or a biologically active substance may be bound. On fusion of the above-stated surface proteins of the polymer particles with a protein which enables direct attachment of a coupling reagent or a biologically active substance, it is essential to ensure in this process that, after fusion with the surface protein of the polymer particle, the functionality of both the surface protein and the fused protein is fully retained.

In one exemplary embodiment, a polymer particle with two FLAG epitopes is fused directly onto the N-terminus of the polymer synthase PhaC1 from *P. aeruginosa*. The FLAG epitopes enable the binding of commercial anti-FLAG mAbs (monoclonal antibodies) (Anti-FLAG M2, Sigma-Aldrich) and then of enzyme markers which are intended to prove the successful performance of the process. In this Example, secondary antibody/alkaline phosphatase conjugates (antimouse alkaline phosphatase, Sigma-Aldrich) are used as the enzyme marker. The activity of the alkaline phosphatase on the surface of the polymer particles is then determined photometrically.

EXAMPLE 6.2.1

Production of a Polymer Particle with a FLAG-PhaC1 Fusion Protein

The following oligonucleotides are used for the production of the FLAG-polymer synthase fusion protein: 5'-tatgactagt gattataaagatgatgatgataaaca-3' and 5'-ta tgtttatcatcatcatctttataatcactagtca-3' (SEQ ID No. 10 and SEQ ID No. 11, SpeI restriction site in bold, FLAG epitope underlined). In order to obtain double-stranded DNA by hybridisation, the two oligonucleotides are mixed together in equimolar quantity (each 10 µM) and incubated for 30 min at room temperature (RT). The double-stranded DNA formed in this manner codes for the FLAG epitope (DYKDDDDK) and has overhanging ends (TA) which are complementary to the overhanging ends of the NdeI restriction site $$\left( \frac{CA^\nabla TATG}{GTAT_\triangle AC} \right).$$

This DNA fragment is hydrolysed with the restriction enzyme NdeI and cloned into the vector pHBR71 (FIG. 10) which has to this end been similarly hydrolysed. The plasmid pBHR71-FLAG (FIG. 13) obtained in this manner contains the gene with SEQ ID No. 12 and imparts expression of a polymer synthase with N-terminal FLAG fusion (this part of the protein now forms the binding domain). Biologically active substances and/or coupling reagents may now be bound by means of this binding domain. The singular SpeI restriction site which is likewise introduced during cloning is additionally available for the insertion of any desired further DNA fragments which code for functional proteins.

The following method is used as an example of the functionality of the above-stated construct. Once the pBHR71-FLAG plasmid has been transformed into *E. coli* strains which already contain the plasmid pBBad-F and exhibit a modified fatty acid metabolism (c.f. Example 3), the polymer particles are expressed. The polymer particles are isolated from the cells by disrupting the cells and are washed three times with PBS buffer (pH 7.5). The polymer particles are then incubated for 30 min at RT with monoclonal anti-FLAG antibodies which bind to the FLAG epitopes. The polymer particles are then rewashed, as already described above, and then incubated with secondary alkaline phosphatase conjugate for 30 min at RT in PBS buffer. After the 30 minutes' incubation, these particles are washed in 0.1 M tris-HCl (pH 8.5) and then 2 mg/ml of p-nitrophenyl phosphate are added to the particle suspension as a substrate for the alkaline phosphatase. The activity of the alkaline phosphatase is measured spectrometrically at 410 nm. Polymer particles which contain a polymer synthase without a binding domain, i.e. without the FLAG epitope, are used as a negative control. Since the added p-nitrophenyl phosphate is not converted in the control, the results of the spectrometric measurements at 410 nm are negative. The mere fact that the polymer particles have actually formed is proof that the incorporation of the FLAG epitope has had no effect on the functionality of the polymer synthase.

This process may also be performed with one of the other above-stated surface proteins of the polymer particles. If two or more surface proteins are simultaneously modified, a plurality of the most varied substances may be bound to the polymer particles, so permitting multifunctionality and making them suitable for many different applications.

While in the previous example a biologically active substance was subsequently bound to the already expressed and formed surface protein of the polymer particle, it is also of course possible to fuse the protein directly with the surface protein and then express it. To this end, the coding sequences of the proteins (for example enzymes) are fused with the C-terminal end of the phaC1 gene of the pBHR71-FLAG plasmid.

DNA fragments are obtained by PCR which in each case code for the protein to be inserted and for the C-terminal fragment of the polymer synthase in order to enable fusion with the phaC1 gene. The two fragments are ligated together by means of a restriction site inserted with overhanging primers. At the 5' end of this hybrid gene, at a distance of 7 nt from the start codon, a ribosomal binding site (GAGGAG) and a restriction site are inserted by means of overhanging primers. If the vector used, such as for example the pBHR71-FLAG vector used in this case, already has a ribosomal binding site, it is no longer necessary additionally to insert a ribosomal binding site. Together with an inserted restriction site at the 3' end of this hybrid gene, purposeful cloning into the expression vector pBHR71-FLAG is now possible. The restriction sites at the 5' and 3' ends of the hybrid gene must be selected such that they do not occur a second time within the hybrid gene, so that cloning into an expression vector can proceed colinearly to the present promoter. In this Example, the lacZ gene from *E. coli* is amplified by means of PCR with primers which contain an SpeI restriction site: 5'-ggactagtatgaccatgattacggattcactggc-3' (SEQ ID No.13, SpeI restriction site in bold) and 5'-ccactagttttttgacaccagaccaactggtaatggtagcg-3' (SEQ ID No. 14, SpeI restriction site in bold). In addition, the stop codon is removed from the sequence of the lacZ gene by using these primers in order to obtain a continuous reading frame. The resultant DNA fragment with SEQ ID No. 15 is cloned directly into the SpeI restriction site of the pHBR71-FLAG plasmid. The fusion protein obtained gave rise to the formation of polymer particles with β-galactosidase activity. The corresponding polymer particles are isolated and β-galactosidase activity is demonstrated under reducing conditions with the substrate o-nitrophenyl-beta-D-galactopyranoside (Calbiochem).

EXAMPLE 7

Stability of the Bond Between the Surface Proteins and the Polymer Core of the Polymer Particles Investigations carried out for the purposes of the invention have revealed that the polymer synthase cannot be detached from the core of the biodegradable polymer particle either by treatment with denaturing reagents, such as for example sodium dodecyl sulfate (SDS), urea, guanidium hydrochloride or dithiothreitol, nor by the use of acidic conditions. This is indicative of the presence of a covalent linkage between the polymer particles and the polymer particle binding domain of the polymer synthase. The elevated stability of the bond enables stable transportation of substances bound to or incorporated into the polymer particles to their target site. The N-terminus fragment of the surface-bound polymer synthase (N-terminus to the beginning of the conserved α/β-hydrolase domain) is extremely variable and may be replaced by functional proteins using genetic engineering methods. In this manner, polymer synthase activity and synthesis of polymer particles are retained (Rehm, B. H. A. et al, Biochem. Biophys. Acta 2002, Vol. 1594, pp. 178-190). As a consequence, surface functionalisation is obtained which exhibits elevated stability. A mixture of different proteins with different binding domains to which the biologically active substances and/or coupling reagents are bound are, if required, applied simultaneously, so giving rise to multifunctionalisation of the polymer particle surface. These proteins are applied in vitro by adding the purified proteins with different binding domains to the synthesis batch or in vivo by expression of the genes in the corresponding microorganism which in each case code for a protein with a binding domain.

EXAMPLE 7.1

Further Possibilities for Modifying the Surface Proteins of the Polymer Particles The C-terminal fragment of the surface protein phasin (PhaP) from *R. eutropha* (amino acid residues from >Ala141) is hydrophilic and may be replaced by functional proteins without preventing anchoring of the phasin via the polymer particle binding domain to the surface of the polymer particles.

This anchoring is based on hydrophobic interactions and is reversible (Hanley, S. Z. et al, FEBS Letters 1999, Vol. 447, pp. 99-105). This C-terminal fragment of the intracellular polymer depolymerases is fused by genetic engineering processes with functional proteins and so enables functionalisation of the surface of the polymer particle by means of subsequent attachment of biologically active substances and/or coupling reagents.

The C-terminus (amino acid residue from >180) of the intracellular polymer depolymerase of *R. eutropha* binds the enzyme to the core of the polymer particles (Saegusa, H. et al., J. Bacteriol. 2001, Vol. 183(1), pp. 94-100). This C-terminal fragment of the intracellular polymer depolymerases is fused by genetic engineering processes with functional proteins and so enables functionalisation of the surface of the polymer particle.

The N-terminus (amino acid residue from <140) of the expression products, bound to the surface of the polymer particles, of the genes phaI and phaF from *Pseudomonas oleovorans* bind the proteins to the polyester core of the polymer particles (Prieto, M. A. et al., J. Bacteriol. 1999, Vol. 181(3), pp. 858-868). This N-terminal fragment of the expression products of the genes phaF and phaI is fused by genetic engineering processes with a functional protein and the resultant binding domain then enables functionalisation of the surface of the polymer particle by attachment of biologically active substances and/or coupling reagents.

EXAMPLE 8

Figure 1:
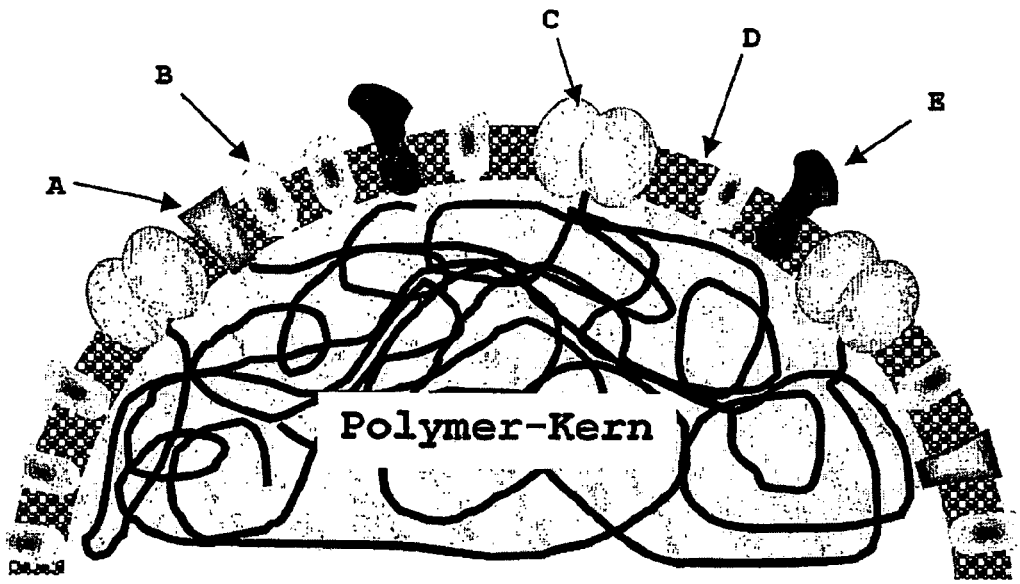
FIG. 1 shows a schematic overview of an in vivo produced biodegradable polymer particle and the proteins and lipids which are bound to the surface.

Covalent Modification of the Surface Proteins of the Polymer Particles with a Coupling Reagent The proteins shown in FIG. 1 on the surface of the biodegradable polymer particles may be treated with specific labelling substances which bind specifically to certain amino acids (for example N-hydroxysuccinimide biotin to lysine). This enables the attachment of biologically active substances, such as for example of biotin by iodoacetamide-mediated linkage to cysteine. Molecules, such as biotin, then effect a further linkage of biologically active substances onto the surface proteins of these polymer particles. These include, for example, avidin or streptavidin which may themselves be bound to enzymes and so permit progressive functionalisation of the surface proteins of the biodegradable polymer particles (Rehm, B. H. A. et al., J. Bacteriol. 1994, Vol. 176, pp. 5639-5647). This functionalisation may proceed by attachment of antibodies or pharmaceutical active ingredients. Molecules with different surface charges may also be attached in order to impart to the polymer particles a specific surface charge which is advantageous for transport through/fusion with certain membranes.

Labelling of lysine residues on the surface proteins of the polymer particles with biotin is achieved by means of n-hydroxysuccinimide biotin. In this experiment, polymer particles which bear the polymer synthase PhaC1 from *P. aeruginosa* are isolated from recombinant *E. coli* which bears the plasmid pHBR71. After isolation, the polymer particles are washed three times in PBS (pH 8.0) washed and n-hydroxysuccinimide biotin (Sigma-Aldrich) is then added to the solution up to a final concentration of 5 mM. The reaction is terminated by washing again after 5 minutes' incubation at 4° C. Detection of the biotin bound to the particle surface is performed with the assistance of the streptavidin-alkaline phosphatase conjugate (Sigma-Aldrich) and o-nitrophenyl phosphate (Calbiochem) as substrate. In the control batch with particles which have not been treated with n-hydroxysuccinimide biotin, the particles do not exhibit alkaline phosphatase activity.

In addition to the examples listed here, there are many other coupling reagents for linking biologically active substances with the assistance of which the surface proteins of the polymer particles produced here may be activated.

The invention claimed is:

1. A process for producing polyhydroxy carboxylate particles having surface-bound proteins, the process comprising:
   A) providing a cell comprising at least one gene that codes for a fusion protein, the fusion protein comprising
      (a) a polymer synthase from a microorganism of the genera *Ralstonia, Alcaligenes, Pseudomonas, Aeromonas*, or *Thiocapsa*, and
      (b) at least one protein selected from an oligopeptide, antibody, non-catalytic protein or enzyme, fused with the N-terminus of the polymer synthase, the polymer synthase comprising a polymer particle binding domain;
   B) cultivating the cell in a culture medium so that the cell produces the fusion protein from the at least one gene and produces polymer particles comprising polyhydroxy carboxylate, wherein the polymer particle binding domain of the fusion protein is bound to a polymer particle; and
   C) separating the polymer particles from the cultivated cells to produce a composition comprising polyhydroxy carboxylate particles having surface-bound proteins.

2. A process according to claim 1, wherein the polymer synthase is from *Ralstonia eutropha, Pseudomonas oleovorans, Pseudomonas putida, Pseudomonas aeruginosa, Aeromonas punctata* or *Thiocapsa pfennigii*.

3. A process according to claim 1, wherein the culture medium comprises at least one hydroxy fatty acid.

4. A process according to claim 1, wherein a hydroxy fatty acid is added to the culture medium in such a quantity that it is sufficient to ensure control of the size of the polymer particles.

5. A process according to claim 1, wherein the cell is a microorganism selected from the genera consisting of *Escherichia, Ralstonia, Alcaligenes, Pseudomonas, Halobiforma Aeromonas*, and *Thiocapsa*.

6. A process according to claim 1, wherein the polymer particles have a diameter of 10 nm to 3 μm.

7. A process according to claim 1, wherein the polymer particles have a diameter of 10 nm to 900 nm.

8. A process according to claim 1, wherein the polymer particles have a diameter of 10 nm to 100 nm.

9. A process according to claim 1, wherein at least one dye is added to the culture medium and incorporated into the particles.

10. A process according to claim 1, further comprising
    D) chemically modifying the polymer synthase by contacting the polymer synthase with a coupling reagent.

11. A process according to claim 1, further comprising
    D) binding a biologically active substance to the fusion protein, wherein the biologically active substance is selected from
    i) dideoxyinosine, floxuridine, 6-mercaptopurine, doxorubicin, daunorubicin, 1-darubicin, cisplatin, methotrexate, taxol, antibiotics, anticoagulants, germicides, antiarrhythmic agents and active ingredient precursors or derivatives thereof, or
    ii) insulin, calcitonin, ACTH, glucagons, somatostatin, somatotropin, somatomedin, parathyroid hormone, erythropoietin, hypothalamic release factors, prolactin, thyroid-stimulating hormone, endophins, enkephalins, vasopressins, non-naturally occurring opiates, superoxide dismutase, antibodies, interferons, asparaginase, arginase, arginine deaminase, adenosine deaminase, ribonuclease, trypsin, chymotrypsin or pepsin, or
    iii) an oligopeptide, antibody, non-catalytic protein or enzyme.

12. A process according to claim 1, wherein the protein is selected from insulin, calcitonin, ACTH, glucagons, somatostatin, somatotropin, somatomedin, parathyroid hormone, erythropoietin, hypothalamic release factors, prolactin, thyroid-stimulating hormone, endophins, enkephalins, vasopressins, non-naturally occurring opiates, superoxide dismutase, antibodies, interferons, asparaginase, arginase, arginine deaminase, adenosine deaminase, ribonuclease, trypsin, chymotrypsin or pepsin.

13. A process according to claim 1, wherein the protein is an antibody.

14. A process according to claim 10, wherein the coupling reagent is selected from the group consisting of bis(2-oxo-3-oxazolydinyl)phosphonic chloride (BOP-Cl), bromotrispyrrolidinophosphonium hexafluorophosphate (PyBroP), benzotriazol-1-yl-oxy-trispyrrolidinophosphonium hexafluorophosphate (PyBOP), n-hydroxysuccinimide biotin, 2-(1H-benzotriazol-1-yl)-1,1,3,3-tetramethyluronium hexafluorophosphate (HBTU), dicyclohexylcarbodiimide, disuccinimidyl carbonate, 1-(3-dimethylaminopropyl)-3-ethylcarbodiimide (EDC), bis(2-oxo-3-oxazolydinyl) phosphine, diisopropylcarbodiimide (DIPC), 2-(1H-benzotrioxazolyl)-1,1,3,3-tetramethyluronium tetrafluoroborate (TBTU), 2-(5-norbornene-2,3-dicarboxyimido)-1,1,3,3-tetramethyluronium tetrafluoroborate (TNTU), para-nitrophenylchloroformate, and O-(n-succinimidyl)-1,1,3,3-tetramethyluronium tetrafluoroborate (TSTU).

15. A process according to claim 1, wherein the cell comprises two or more of the at least one gene that codes for a fusion protein.

16. A process according to claim 1, wherein the cell comprises three or more of the at least one gene that codes for a fusion protein.

17. A process according to claim 1, wherein one or more of the surface-bound proteins are removed from the polymer particles.

18. A process according to claim 1, wherein the composition consists essentially of polymer particles having surface-bound proteins.

19. A method of binding a second protein comprising
  A) providing a composition of polymer particles produced by a method according to claim 1, wherein optionally a coupling reagent is bound to the fusion protein, and
  B) contacting the composition with a sample comprising a second protein selected from an oligopeptide, antibody, non-catalytic protein or enzyme so that the protein or the coupling reagent binds the second protein.

20. A process according to claim 1, wherein the cell further comprises one or more genes that code for one or more additional fusion proteins, the one or more additional fusion proteins comprising
  (a) a polymer particle binding domain, or
  (b) a protein involved in the formation of the polymer particles, the protein comprising a polymer particle binding domain, the additional fusion protein further comprising
  (i) at least one protein selected from an oligopeptide, antibody, non-catalytic protein or enzyme, or
  (ii) at least one binding domain capable of binding one or more proteins or one or more coupling reagents, wherein the protein is selected from an oligopeptide, antibody, non-catalytic protein or enzyme, or
  (iii) at least one protein and at least one binding domain capable of binding one or more biologically active substances or one or more coupling reagents, wherein the protein is selected from an oligopeptide, antibody, non-catalytic protein or enzyme, or
  (iv) a combination thereof.

21. A process according to claim 5, wherein the microorganism is selected from the group consisting of *Ralstonia eutropha, Alcaligenes latus, Escherichia coli, Pseudomonas fragi, Pseudomonas putida, Pseudomonas oleovorans, Pseudomonas aeruginosa, Pseudomonas fluorescens, Halobiforma haloterrestris, Aeromonas punctata* and *Thiocapsa pfennigii*.

22. A process according to claim 20, wherein the at least one gene that codes for a protein involved in the formation of polymer particles is selected from the group consisting of a gene coding for a phaA thiolase, a gene coding for a phaB ketoacyl reductase, a gene coding for a polymer depolymerase, a gene coding for a polymer regulator, a gene coding for a polymer synthase, and a gene coding for a particle size-determining protein, or a combination thereof.

* * * * *

UNITED STATES PATENT AND TRADEMARK OFFICE
CERTIFICATE OF CORRECTION

PATENT NO. : 7,622,277 B2
APPLICATION NO. : 10/525955
DATED : November 24, 2009
INVENTOR(S) : Bernd Helmut Adam Rehm It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 147 days.

Signed and Sealed this

Twenty-sixth Day of October, 2010

David J. Kappos
*Director of the United States Patent and Trademark Office*